(12) United States Patent
Wei et al.

(10) Patent No.: US 10,166,104 B2
(45) Date of Patent: Jan. 1, 2019

(54) CALCIUM PHOSPHATE POLYMER COMPOSITE AND METHOD

(71) Applicants: Teleflex Medical Incorporated, Morrisville, NC (US); The University of Connecticut, Farmington, CT (US)

(72) Inventors: Mei Wei, Coventry, CT (US); James R. Olson, Norwich, CT (US); Montgomery T. Shaw, Coventry, CT (US)

(73) Assignees: TELEFLEX MEDICAL INCORPORATED, Morrisville, NC (US); THE UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 15/421,983

(22) Filed: Feb. 1, 2017

(65) Prior Publication Data

US 2017/0348104 A1 Dec. 7, 2017

Related U.S. Application Data

(63) Continuation of application No. 11/790,345, filed on Apr. 25, 2007.

(Continued)

(51) Int. Cl.
*A61L 27/46* (2006.01)
*A61F 2/28* (2006.01)
(Continued)

(52) U.S. Cl.
CPC ............ *A61F 2/28* (2013.01); *A61F 2/30965* (2013.01); *A61L 27/20* (2013.01); *A61L 27/425* (2013.01);
(Continued)

(58) Field of Classification Search
CPC .................................................... A61L 27/46
See application file for complete search history.

(56) References Cited

U.S. PATENT DOCUMENTS

| 3,463,158 A | 8/1969 | Schmitt et al. |
| 3,620,218 A | 11/1971 | Schmitt et al. |

(Continued)

FOREIGN PATENT DOCUMENTS

| JP | 8215299 | 8/1996 |
| JP | 2004-160157 | 6/2004 |

(Continued)

OTHER PUBLICATIONS

"Analysis of the Initial Burst of Drug Release Coupled with Polymer Surface Degradation," J-W. Lee, et al., Pharmaceutical Research, vol. 20, No. 2, Feb. 2003.

(Continued)

*Primary Examiner* — Michael F Pepitone
(74) *Attorney, Agent, or Firm* — Baker Hostetler LLP

(57) ABSTRACT

A bone-repair composite includes a core and a sheath. The core is a first primary unit including a combination of a first set of yarns coated with a calcium phosphate mineral layer. The first set of yarns being made from a first group of one or more polymers. The sheath is a second primary unit a combination of a second set of yarns or one or more polymer coatings. The second set of yarns being made from a second group of one or more polymers, wherein the composite is made by covering the core with the sheath, and the composite is compression molded to allow the sheath to bond to the core. The bone-repair composite has a bending modulus comparable to that of a mammalian bone, such that the ratio of the core to the sheath is provided to maximize the mechanical strength of the bone-repair composite to mimic the mammalian bone.

6 Claims, 15 Drawing Sheets

(a)

Related U.S. Application Data

(60) Provisional application No. 60/794,518, filed on Apr. 25, 2006.

(51) Int. Cl.
*A61F 2/30* (2006.01)
*A61L 27/20* (2006.01)
*A61L 27/42* (2006.01)
*A61F 2/46* (2006.01)

(52) U.S. Cl.
CPC ......... *A61F 2/3094* (2013.01); *A61F 2/30767* (2013.01); *A61F 2/468* (2013.01); *A61F 2002/2817* (2013.01); *A61F 2002/30032* (2013.01); *A61F 2002/30062* (2013.01); *A61F 2002/30224* (2013.01); *A61F 2002/30235* (2013.01); *A61F 2002/30293* (2013.01); *A61F 2002/30677* (2013.01); *A61F 2002/30914* (2013.01); *A61F 2002/30957* (2013.01); *A61F 2210/0004* (2013.01); *A61F 2230/0069* (2013.01); *A61F 2230/0091* (2013.01); *A61F 2250/003* (2013.01); *A61F 2310/00293* (2013.01); *A61F 2310/00365* (2013.01); *A61F 2310/00796* (2013.01); *A61L 27/46* (2013.01); *A61L 2430/02* (2013.01)

(56) References Cited

U.S. PATENT DOCUMENTS

| | | |
|---|---|---|
| 3,636,956 A | 1/1972 | Schneider |
| 3,739,773 A | 6/1973 | Schmitt et al. |
| 4,049,763 A | 9/1977 | Mineo et al. |
| 4,097,935 A | 7/1978 | Jarcho |
| 4,111,294 A | 9/1978 | Carpenter et al. |
| 4,186,448 A | 2/1980 | Brekke |
| 4,192,021 A | 3/1980 | Deibig et al. |
| 4,279,249 A | 7/1981 | Vert et al. |
| 4,329,743 A | 5/1982 | Alexander et al. |
| 4,338,926 A | 7/1982 | Kummer et al. |
| 4,345,339 A | 8/1982 | Müller et al. |
| 4,365,357 A | 12/1982 | Draenert |
| 4,623,553 A | 11/1986 | Ries et al. |
| 4,629,464 A | 12/1986 | Takata et al. |
| 4,659,617 A | 4/1987 | Fuji et al. |
| 4,698,375 A | 10/1987 | Dorman et al. |
| 4,736,500 A | 4/1988 | Goineau |
| 4,743,257 A | 5/1988 | Törmälä et al. |
| 4,755,184 A | 7/1988 | Silverberg |
| 4,820,664 A | 4/1989 | Fain |
| 4,836,994 A | 6/1989 | Inoue et al. |
| 4,849,193 A | 7/1989 | Palmer et al. |
| 4,904,257 A | 2/1990 | Mori et al. |
| 4,917,702 A | 4/1990 | Scheicher et al. |
| 4,963,151 A | 10/1990 | Ducheyne et al. |
| 4,965,039 A | 10/1990 | Schuetz |
| 4,968,317 A | 11/1990 | Törmälä et al. |
| 5,047,031 A | 9/1991 | Constantz |
| 5,053,212 A | 10/1991 | Constantz et al. |
| 5,084,051 A * | 1/1992 | Tormala ............. A61L 31/129 428/688 |
| 5,092,890 A | 3/1992 | Pohlemann et al. |
| 5,134,009 A | 7/1992 | Ichitsuka et al. |
| 5,164,187 A | 11/1992 | Constantz et al. |
| 5,196,212 A | 3/1993 | Knoblach |
| 5,263,985 A | 11/1993 | Bao et al. |
| 5,397,358 A | 3/1995 | Wenner et al. |
| 5,425,769 A | 6/1995 | Snyders, Jr. |
| 5,427,754 A | 6/1995 | Nagata et al. |
| 5,492,697 A | 2/1996 | Boyan et al. |
| 5,652,056 A | 7/1997 | Pepin |
| 5,665,120 A | 9/1997 | Ohtsuka et al. |
| 5,741,600 A | 4/1998 | Olson |
| 5,766,618 A | 6/1998 | Laurencin et al. |
| 5,783,217 A | 7/1998 | Lee et al. |
| 5,846,356 A | 12/1998 | Vyakamam et al. |
| 6,013,591 A | 1/2000 | Ying et al. |
| 6,025,285 A | 2/2000 | Vyakamam et al. |
| 6,027,742 A | 2/2000 | Lee et al. |
| 6,039,762 A | 3/2000 | McKay |
| 6,203,573 B1 | 3/2001 | Walter et al. |
| 6,214,008 B1 | 4/2001 | Illi |
| 6,232,384 B1 | 5/2001 | Hyon |
| 6,255,359 B1 | 7/2001 | Agrawal et al. |
| 6,287,341 B1 | 9/2001 | Lee et al. |
| 6,384,197 B1 | 5/2002 | Weis et al. |
| 6,409,764 B1 | 6/2002 | White et al. |
| 6,511,511 B1 * | 1/2003 | Slivka .............. A61F 2/30756 623/16.11 |
| 6,511,748 B1 | 1/2003 | Barrows |
| 6,521,246 B2 | 2/2003 | Sapieszko et al. |
| 6,537,589 B1 | 3/2003 | Chae et al. |
| 6,558,709 B2 | 5/2003 | Higham |
| 6,591,197 B2 | 7/2003 | Trudeau et al. |
| 6,596,296 B1 | 7/2003 | Nelson et al. |
| 6,599,516 B1 | 7/2003 | Knaack |
| 6,602,293 B1 | 8/2003 | Biermann et al. |
| 6,620,287 B2 | 9/2003 | Cass |
| 6,685,957 B1 | 2/2004 | Bezemer et al. |
| 6,719,793 B2 | 4/2004 | McGee |
| 6,747,121 B2 | 6/2004 | Gogolewski |
| 6,767,928 B1 | 7/2004 | Murphy et al. |
| 6,783,712 B2 | 8/2004 | Slivka et al. |
| 6,786,908 B2 | 9/2004 | Hover et al. |
| 6,793,725 B2 | 9/2004 | Chow et al. |
| 6,821,528 B2 | 11/2004 | Scott et al. |
| 6,844,063 B2 | 1/2005 | Matsui et al. |
| 6,863,899 B2 | 3/2005 | Koblish et al. |
| 6,887,272 B2 | 5/2005 | Shinomiya et al. |
| 6,887,488 B2 | 5/2005 | Cui et al. |
| 6,908,466 B1 | 6/2005 | Bonutti et al. |
| 6,949,251 B2 | 9/2005 | Dalal et al. |
| 6,955,716 B2 | 10/2005 | Xu et al. |
| 6,972,130 B1 | 12/2005 | Lee et al. |
| 6,974,862 B2 | 12/2005 | Ringeisen et al. |
| 7,018,460 B2 | 3/2006 | Xu et al. |
| 7,022,522 B2 | 4/2006 | Guan et al. |
| 7,045,105 B2 | 5/2006 | Lagow |
| 7,049,348 B2 | 5/2006 | Evans et al. |
| 7,060,287 B1 | 6/2006 | Hubbard et al. |
| 7,067,577 B2 | 6/2006 | Aramaki et al. |
| 7,189,413 B2 | 3/2007 | Calias et al. |
| 2004/0054372 A1 * | 3/2004 | Corden ............. A61L 27/44 606/77 |
| 2005/0149118 A1 | 7/2005 | Koyfman et al. |
| 2005/0226904 A1 | 10/2005 | Choi et al. |

FOREIGN PATENT DOCUMENTS

| | | | |
|---|---|---|---|
| JP | 2004-243125 | 9/2004 | |
| WO | 02/100331 A2 | 12/2002 | |
| WO | WO 2005018698 A1 * | 3/2005 | ............... A61F 2/28 |

OTHER PUBLICATIONS

"Apatite Formation on Surfaces of Ceramics, Metals and Polymers in Body Environment," T. Kokubo, Acta mater, vol. 46, No. 7, pp. 2519-2527, 1998.

"Apatite-forming ability of CaO-containing titania," M. Wei, et al., Biomaterials 23 (2002) 167-172.

"Bionert, biodegradable and injectable polymeric matrix composites for hard tissue replacement: state of the art and recent developments," J. Mano, et al., Composites Science and Technology 64 (2004) 789-817.

"Bioinspired Growth of Crystalline Carbonate Apatite on Biodegradable Polymer Substrata," W. Murphy, et al., J. Am. Chem. Soc., vol. 124, No. 9, 2002.

"Biomimetic coprecipitation of calcium phosphate and bovine serum albumin on titanium alloy," Y. Liu, et al., Apr. 24, 2001, John Wiley & Sons, Inc.

(56) References Cited

OTHER PUBLICATIONS

"Bioresorbable devices made of forged composites of hydroxyapatite (HA) particles and poly-L-lactide (PLLA): Part I. Basic Characteristics," Y. Shikinami, et al., Biomaterials 20 (1999) 859-877.
"Cell Culture Test of TCP/CPLA Composite," Masanori Kikuchi, et al., Mar. 25, 1998, John Wiley & Sons, Inc.
"Coating of an apatite layer on polyamide films containing sulfonic groups by a biomimetic process," T. Kawai, et al., Biomaterials 25 (2004) 4529-4534.
"Comparison of planar inductively coupled plasma etching of GaAs in BCI3, BCI3/Ar, and BCI3/Ne," J.W. Lee, et al., Applied Surface Science 233 (2004) 402-410.
"Composition and structure of the apatite formed on PET substrates in SBF modified with various ionic activity products," H-M Kim, et al., Jan. 13, 1999, John Wiley & Sons, Inc.
"Control of Crystal Nucleation and Growth of Calcium Carbonate by Synthetic Substrates," K. Naka, et al., Chem. Mater., 2001, 13, 3245-3259.
"Controlled release by biodegradable hydrogels enhances the ectopic bone formation of bone morphogenetic protein," M. Yamamoto, et al., Biomaterials 24 (2003) 4375-4383.
"Crystallization of Hydroxyapatite on Polymers," E. Dalas, et al., Langmuir 1991, 7, 1822-1826.
"Degradation and release profile of microcapsules made of poly[L-lactic acid-co-L-lysine(Z)]," T. Kidchob, et al., Journal of Controlled Release 54 (1998) 283-292.
"Dependence of Mesenchymal Cell Responses on Duration of Exposure to Bone Morphogenetic Protein-2 In Vitro," D. Puleo, Journal of Cellular Physiology 173: 93-101 (1997).
"Deposition of bone-like apatite on silk fiber in a solution that mimics extracellular fluid," A. Takeuchi, et al., Journal of Biomedical Materials Research Part A, vol. 65, No. 2, Mar. 24, 2003, pp. 283-289.
"Dual growth factor delivery and controlled scaffold degradation enhance in vivo bone formation by transplanted bone marrow stromal cells," C. Simmons, et al., Bone 35 (2004) 562-569.
"Effects of transforming growth factor-beta 1 (TGF-β1) on in vitro mineralization of human osteoblasts on implant materials," H. Zhang, et al., Biomaterials 24 (2003) 2013-2020.
"Enhancement of Bone Growth by Sustained Delivery of Recombinant Human Bone Morphogenetic Protein-2 in a Polymeric Matrix," B.H. Woo, et al., Pharmaceutical Research, vol. 18, No. 12, Dec. 2001.
JJ "Evaluation of cytocompatibility and bending modulus of nanoceramic/polymer composites," A. McManus, et al., Aug. 26, 2004, Wiley Periodicals, Inc.
"Hierarchically Ordered Oxides," P. Yang, et al., Science, vol. 282, Dec. 18, 1998.
"Hydroxyapatite-coated tendon chitosan tubes with adsorbed laminin peptides facilitate nerve regeneration in vivo," S. Itoh, et al., Brain Research 993 (2003) 111-123.
"Hydroxyapatite/poly(ε-caprolactone) composite coatings on hydroxyapatite porous bone scaffold for drug delivery," H-W. Kim, et al., Biomaterials 25 (2004) 1279-1287.
"Hydroxyapatite deposition by alternating soaking technique on poly(vinyl alcohol)-coated polyethylene films," T. Serizawa, et al., J. Biomater. Sci. Polymer Edn, vol. 12, No. 12, pp. 1293-1301 (2001).
"In vitro and in vivo evaluation of taxol release from poly(lactic-co-glycolic acid) microspheres containing isopropyl myristate and degradation of the microspheres," Y.M. Wang, et al., Journal of Controlled Release 49 (1997) 157-166.
"In Vitro Degradation and Release Profiles of Poly-DL-Lactide-Poly(ethylene glycol) Microspheres with Entrapped Proteins," X. Li, et al., Journal of Applied Polymer Science, vol. 78, pp. 140-148 (2000).
"In vitro effects of combined and sequential delivery of two bone growth factors," A.T. Raiche, et al., Biomaterials 25 (2004) 677-685.
"In vitro mineralization of gelatin-polyacrylic acid complex matrices," A. Bigi, et al., J. Biomater. Sci. Polymer Edn, vol. 15, No. 3, pp. 243-254 (2004).
"Localized delivery of growth factors for bone repair," V. Luginbuehl, et al., European Journal of Pharmaceutics and Biopharmaceutics 58 (2004) 197-208.
"Locally delivered rhBMP-2 enhances bone ingrowth and gap healing in a canine model," D.R. Sumner, et al., Journal of Orthopaedic Research 22 (2004) 58-65.
"The Material Bone: Structure-Mechanical Function Relations," S. Weiner, et al., Annu. Rev. Mater. Sci., 1998, 28:271-98.
"Optimising the bioactivity of alkaline-treated titanium alloy," M. Wei, et al., Materials Science and Engineering C 20 (2002) 125-134.
"Preparation and characterization of apatite deposited on silk fabric using an alternate soaking process," T. Furuzono, et al., Sep. 20, 1999, John Wiley & Sons, Inc.
"Protein release kinetics of a biodegradable implant for fracture non-unions," C.M. Agrawal, et al., Biomaterials 16 (1995) 1255-1260.
"Release of mifepristone from biodegradable matrices: experimental and theoretical evaluations," A. Charlier, et al., International Journal of Pharmaceutics 200 (2000) 115-120.
"Self-Assembly and Mineralization of Peptide-Amphiphile Nanofibers," J. Hartgerink, et al., Science, vol. 294, Nov. 23, 2001.
"Structural modeling of drug release from biodegradable porous matrices based on a combined diffusion/erosion process," V. Lemaire, et al., International Journal of Pharmaceutics 258 (2003) 95-107.
"Surface functional group dependence on apatite formation on self-assembled monolayers in a simulated body fluid," M. Tanahashi, et al., Journal of Biomedical Materials Research, vol. 34, pp. 305-315 (1997).
"Synthetic biodegradable polymers as orthopedic devices," J. Middleton, et al., Biomaterials 21 (2000) 2335-2346.
"Templating and Supersaturation-Driven Anti-Templating: Principles of Biomineral Architecture," X. Liu, et al., J. Am Chem. Soc., vol. 125, pp. 888-895, 2003.
"Ultrastructural study of an apatite layer formed by a biomimetic process and its bonding to bone," M. Tanahashi, et al., Biomaterials 17 (1996) 47-51.
"The use of OP-1 in femoral impaction grafting in a sheep model," M. McGee, et al., Journal of Orthopaedic Research 22 (2004) 1008-1015.
Yuan, et al., "Formation of bone-like apatite on poly(L-lactic acid) fibers by a biomimetic process," Journal of Biomedical Materials Research, vol. 57, No. 1, Jun. 14, 2001, pp. 140-150.
Kothapalli, et al., "Fabrication of Novel Calcium Phosphate/Poly (lactic acid) Fiber Composites," Journal of Biomedical Materials Research Part B: Applied Biomaterials, vol. 48, Apr. 23, 2007, pp. 89-97.
European Search Report, Application No. 077560463.4 (PCT/US2007/10114), dated Apr. 6, 2011.

* cited by examiner

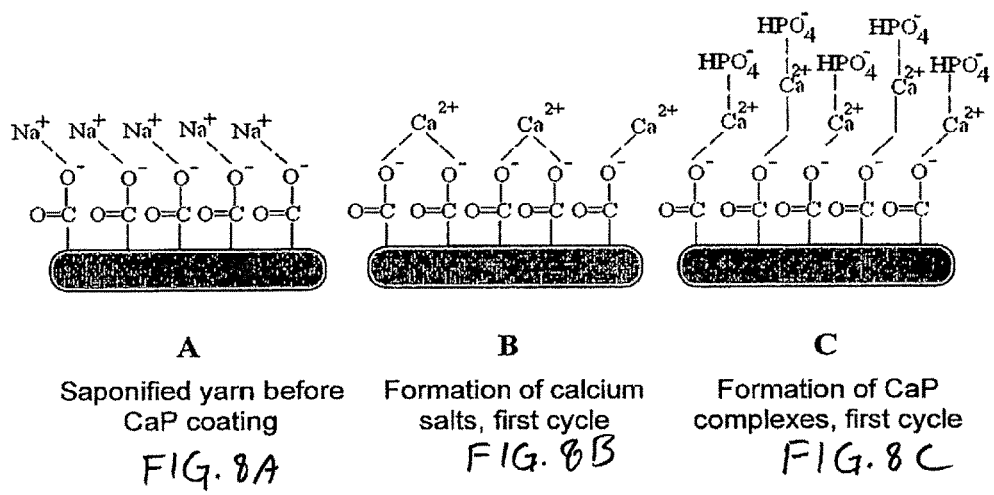
A  
Saponified yarn before CaP coating  
FIG. 8A
B  
Formation of calcium salts, first cycle  
FIG. 8B
C  
Formation of CaP complexes, first cycle  
FIG. 8C
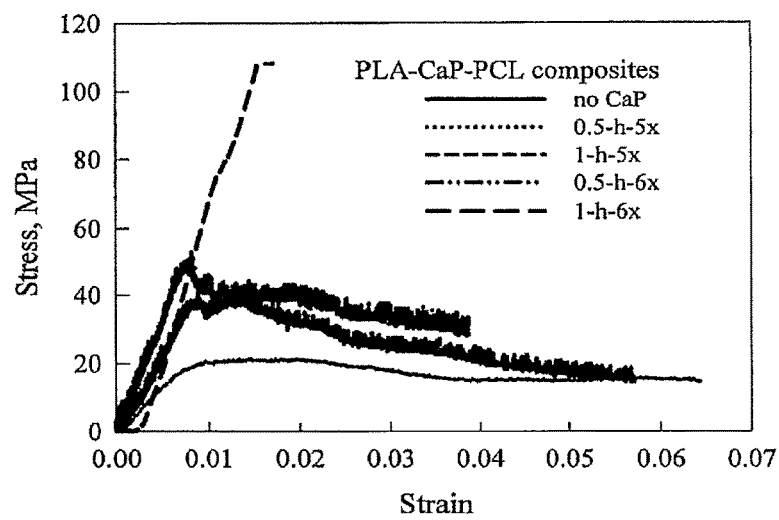
FIG. 9

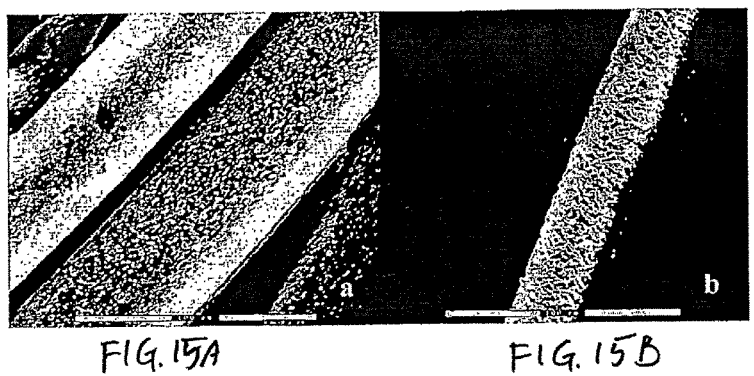
FIG. 15A    FIG. 15B
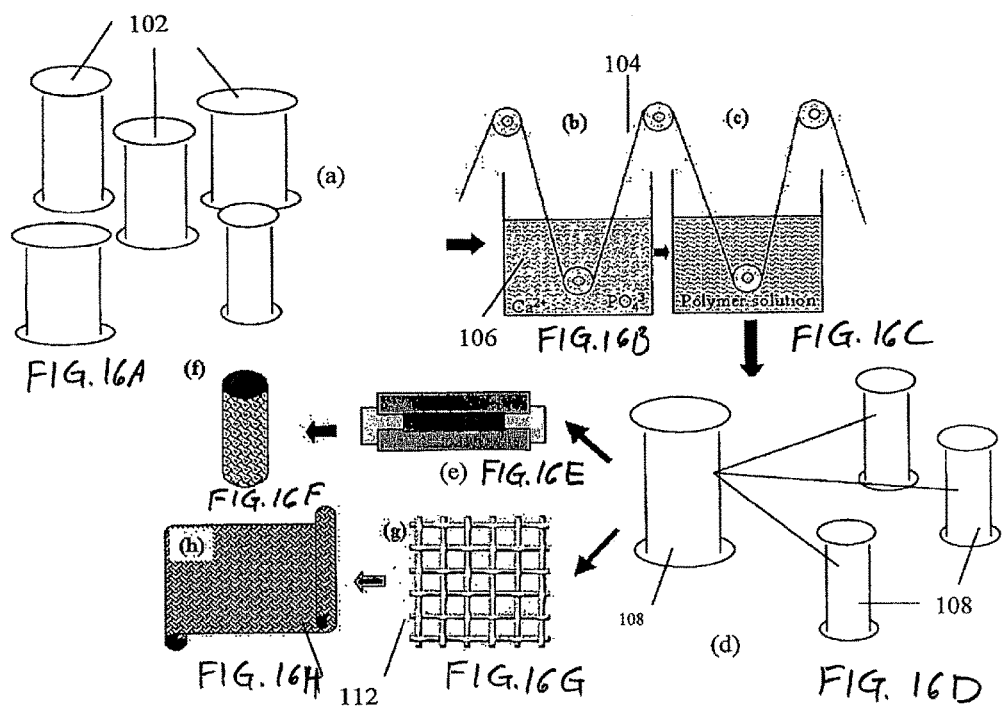

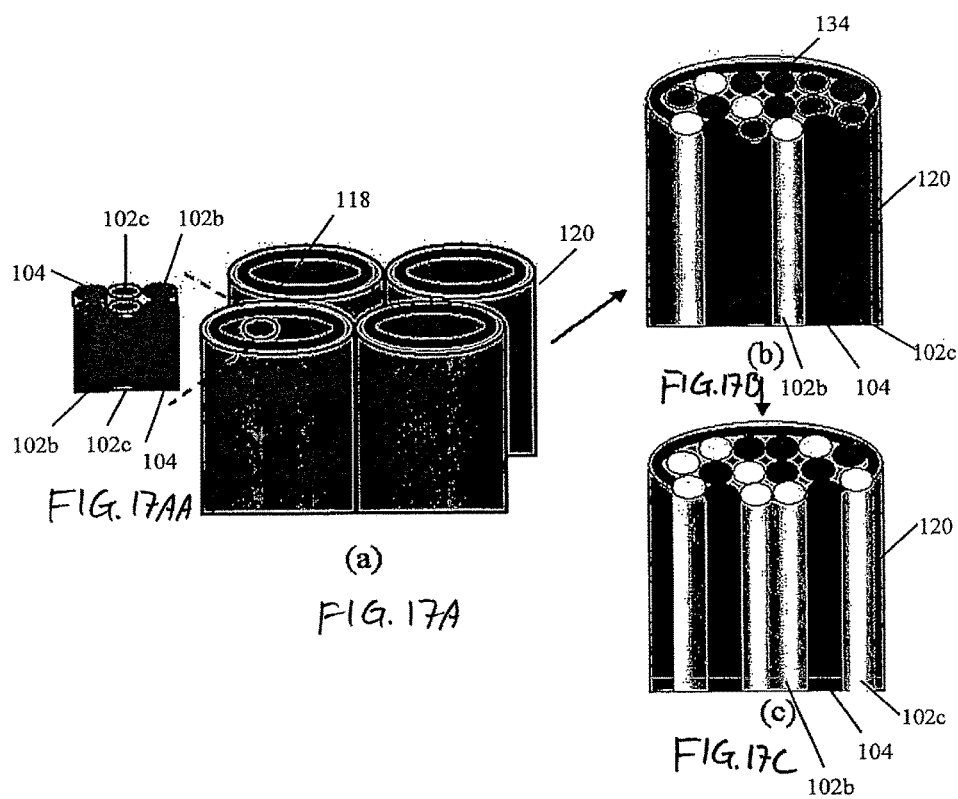
FIG. 17AA
FIG. 17A (a)
FIG. 17B (b)
FIG. 17C (c)
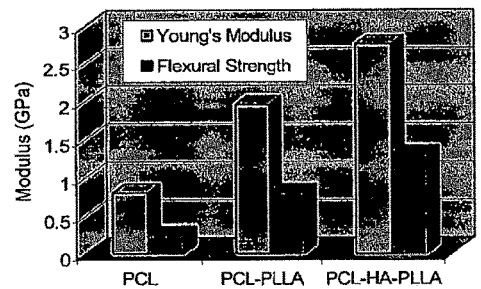
FIG. 18

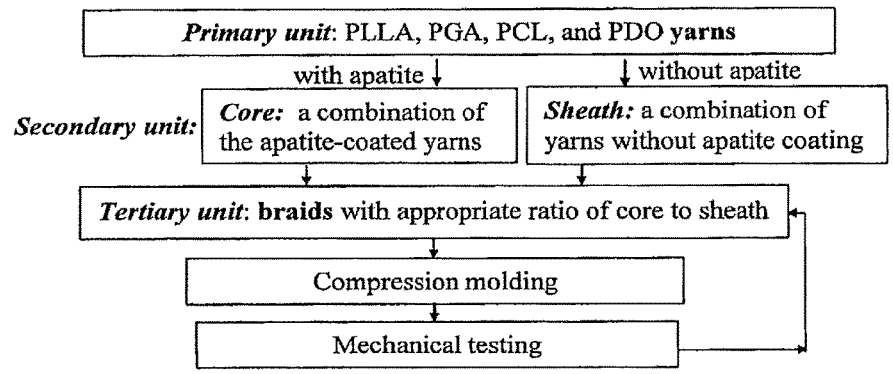
FIG. 23
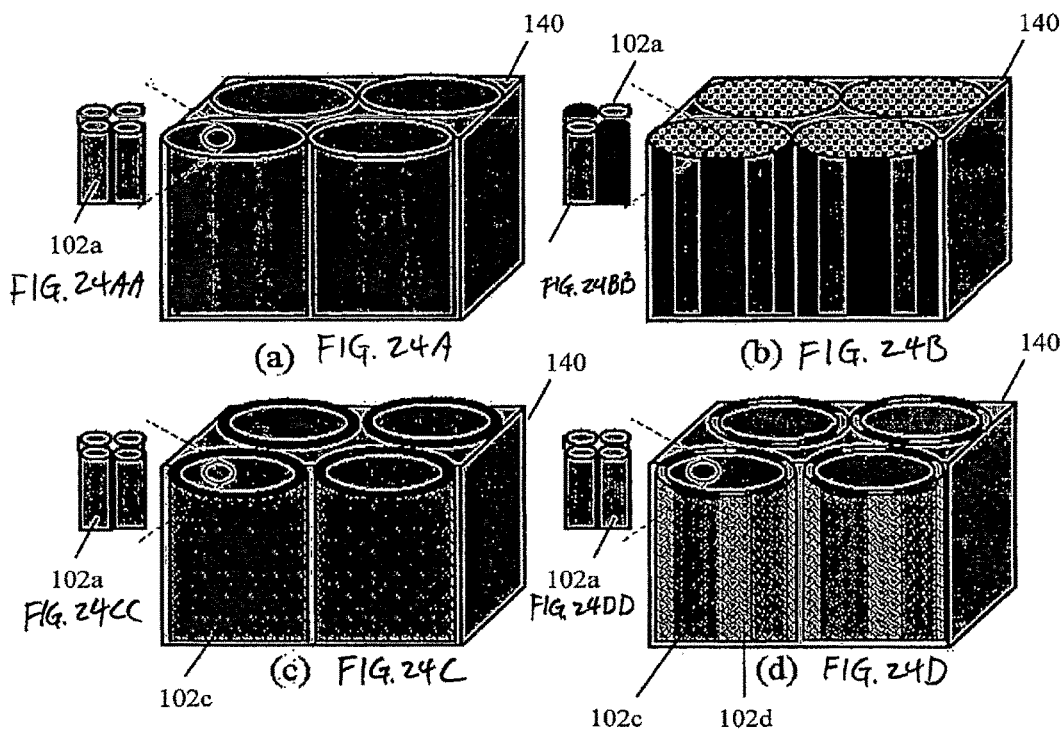
(a) FIG. 24A  (b) FIG. 24B
(c) FIG. 24C  (d) FIG. 24D

CALCIUM PHOSPHATE POLYMER COMPOSITE AND METHOD

CROSS-REFERENCE TO RELATED APPLICATIONS

This application is a continuation of U.S. patent application Ser. No. 11/790,345; filed Apr. 25, 2007 entitled CALCIUM PHOSPHATE POLYMER COMPOSITE AND METHOD and claims priority to provisional U.S. patent application entitled, "CALCIUM PHOSPHATE POLYMER COMPOSITE," filed Apr. 25, 2006, having a Ser. No. 60/794,518, the disclosures of which are hereby incorporated by reference, in their entireties.

FIELD OF THE INVENTION

The present invention relates generally to biomaterials for bone replacement. More particularly, the present invention relates to a mineral polymer composite.

BACKGROUND OF THE INVENTION

Over 10 million Americans carry at least one major implanted medical device in their body. Among these implants, bone fracture and damage cases constitute a large proportion, and result in more than 1.3 million bone-repair procedures per year in the USA. In general, bone tissue has the capability of postnatal self-construction. However, in severe pathological situations such as complicated fractures, trauma, bone tumors, congenital defects or spinal fusion, the damaged bone will not form or regenerate spontaneously. To repair the damaged bone, autografts, long-considered the gold standard in bone grafting, have problems of resource limitation and morbidity associated with graft harvest, while the allogenic bones from tissue banks have the disadvantages of immune response due to genetic differences and the risk of inducing transmissible diseases. As a result, various synthetic materials have been developed for bone repair applications.

Since the discovery of osteoinductivity Bone Morphogenetic Proteins (BMPs), the bone repair process has been greatly advanced by applying these proteins for therapeutic use. Some of the BMPs, such as BMP-2, in particular have been well studied and have gained interest as therapeutic agents. BMP-2 induces bone formation in vivo by stimulating differentiation of mesenchymal stem cells toward an osteoblastic lineage, thereby increasing the number of differentiated osteoblasts capable of forming bone. The stimulation of BMP on osteoblast differentiation plays a major role in bone healing. Recently, regulatory agencies in the U.S., Europe, Canada and Australia have approved devices containing BMP-2 and BMP-7 as bone-graft substitutes for the treatment of long bone fractures and interbody fusions of the spine. Despite its strong osteoinductive activity, clinical use of BMP-2 has been hampered by the lack of suitable delivery systems. An efficacious delivery system is needed to have sustained BMP release with appropriate dosing at the defect site. Both in vitro and in vivo studies have suggested that a dose response can be produced to affect the cell activities and the bone formation rate. The longer the release time of the BMP-2, the more fully the cells expressed sustained osteoblastic traits in vitro and the more bone formation in vivo. Thus, there is a pressing need to develop a synthetic carrier that has high initial structural integrity and sustained release of single or multiple agents known to induce bone regeneration. At the same time, these materials should undergo slow controlled resorption, eliminating the need for subsequent surgical removal. Such materials could have great clinical value when incorporated into medical devices.

Metallic materials have been widely used due to their high mechanical strength. However, the high strength of metallic implants normally reduces the stress in the surrounding materials (stress shielding), which weakens the adjacent bones. In addition, metal implants may release ions, which can cause adverse tissue reactions.

Furthermore, bone fixation devices composed of metal have a number of known problems such as stress shielding at the implant site and possible removal in a second surgery. Thus, absorbable implants for bone fixation have been developed to provide strength for healing and biodegradation for eventual replacement of the device with bone tissue. Design of bone fixation devices must consider tensile and bending strengths, their respective elastic modulus, biocompatibility, ability to support new bone growth, 3-dimensional structure and density, porosity and rate of degradation. Natural bone has a bending modulus in the range of about 3 to 30 MPa. An optimum bone fixation device is expected to be near or in this range for desired clinical utility. Although this has been generally recognized as a factor it has not been successfully put into practice.

Current devices are made from absorbable polymers and/or minerals, and often in a composite form. The minerals are most often calcium phosphate compounds. The absorbable polymers are most often synthetic aliphatic polyesters, polyethers, polycarbonates or their combinations. A problem with absorbable polymers is that in non-fiber form their strength is low. Absorbable fibers have much improved tensile strength, but suffer from low bending modulus. A problem with calcium phosphates is that despite high hardness, they are brittle. Thus, the right combination of these components is lacking in the current absorbable bone fixation devices.

In contrast to metallic implants, polymer-based implants have a more stable bone/implant interface during physiological loading. In addition, some polymers are biodegradable in vivo, and can be gradually replaced by living tissue, which is the best repair for defects. Unfortunately, polymers have relatively poor mechanical properties, which greatly restrict their usefulness in many applications. A second drawback arises because nearly all polymeric materials are bioinert, so they are consequently not osteoconductive, resulting in poor surface continuity. In order to achieve the osteoconductivity of the polymeric material, calcium phosphate, a bioactive ceramic material, is added to the polymer matrix to produce calcium phosphate-reinforced polymer composites. Most of these composites still have the low mechanical strength as pure polymer materials. Thus, there is a pressing need to identify novel calcium phosphate-reinforced polymer composites with sufficient mechanical strength for load-bearing skeletal implants.

Calcium phosphate (CaP)-reinforced polymer composites were originally envisioned as biomaterials for bone replacement on the basis of producing appropriate mechanical compatibility, as well as the required biocompatibility. According to published reports, up to 50 wt % of CaP was incorporated into the polymer matrix to achieve sufficiently high values of elastic modulus. Unfortunately, the composites lacked sufficient toughness for use in different applications.

There are a number of factors that influence the design of a skeletal implant. Structurally, bone is a nano carbonated hydroxyapatite (calcium phosphate) reinforced fibrous collagen composite. The calcium phosphate crystals, which take the form of platelets, are embedded within the collagen fiber matrix and are aligned along the fibers. These mineral-containing fibrils are arranged into lamellar sheets, which run helically with respect to the major axis of the cylindrical osteons. The preferential orientation of bone minerals and the interfacial bonding between the mineral and collagen fibers play an important role in determining the overall mechanical performance of the bone. Thus, the stiffness or average elastic modulus of bone is variable, but lies in the range of 3 to 30 GPa. At least three basic features must be addressed in device design: the property match between bone and the material of construction, the interface between this material and the bone, and the long-term stability of the overall assembly in the in-vivo environment.

Natural bone development and regeneration are regulated by a series of growth factors, so it is often desirable to deliver more than one of multiple exogenous growth factors during bone formation and repair. It has been found that a combination of BMP-2 and transforming growth factor-β (TGF-β) greatly enhanced bone healing compared to BMP-2 or TGF-β delivered separately. Unfortunately, most drug delivery systems are not able to systematically control the delivery multiple growth factors. It would be advantageous if sequential delivery can be designed into a carrier system. To achieve a maximum benefit, it is best to mimic nature's delivery of multiple growth factors in a programmed, sequential manner. Thus, the type and delivery kinetics of growth factors, and the type of carrier material all play a decisive role in the therapeutic success of any bone-repair process.

Therefore, a novel CaP-reinforced biodegradable polymer continuous-yarn composite is needed that features a biomimetic coating on the yarns to gain a high modulus. Furthermore, a new calcium fibrous polymer composite with a Young's modulus matched to natural bone, sufficient mechanical strength to support reasonable loads during the healing process, excellent biocompatibility, capability of controlled release of drugs, good osteoconductivity and osteoinductivity to enhance both bone formation and ingrowth, appropriate degradation rate, and capability of being replaced by natural bone in the long-term, is needed. Furthermore, it is desirable to provide a calcium mineral coated biodegradable yarn composite.

SUMMARY OF THE INVENTION

The foregoing needs are met, to a great extent, by the present invention, wherein one embodiment provides a new bone-repair synthetic composite material, which has sufficient mechanical strength during the bone healing process, and provides a long-term localized release of more than one growth factor.

The novel calcium phosphate/polymer fiber composite consists of many components with different degradation rates, such as polymer fibers, calcium phosphate, and low-melting temperature polymer coatings, all of which can be used as drug carrier materials. The biodegradable polymer fibers, including poly(L-lactic) acid (PLLA), polyglycolic acid (PGA), polydioxanone (PDO) and/or catgut, are coated with a thin layer of calcium phosphate. They can then be braided using a method according to one embodiment to fabricate sutures. The braids are coated with a layer of low-melting temperature biodegradable polymer. In one embodiment, the treated braids are subjected to compression molding and formed into bar-shaped composites. In addition, braids are woven or knitted to form sheet-shaped composites. The unique design and fabrication sequence make it possible to use the composite as a sophisticated drug delivery system featuring designed release of more than one drug. The drugs are those that are suitable for varied bone repair applications, such as long-bone repair, spinal fusion, sternal bone closure, maxillofacial fixation and the like, although other drugs such as antibiotics are also feasible.

In accordance with one embodiment of the invention, a bone-repair composite is provided. The bone-repair composite includes a core and a sheath. The core is a first primary unit including a combination of a first set of yarns coated with a calcium phosphate compound layer. The first set of yarns being made from a first group of one ore more polymers. The sheath is a second primary unit including a combination of a second set of yarns. The second set of yarns being made from a second group of one or more polymers, wherein the composite is made by covering the core with the sheath, and the composite is compression molded to allow the sheath to bond to the core. The bone-repair composite has a bending modulus comparable to that of a mammalian bone, wherein the ratio of the core to the sheath is provided to maximize the mechanical strength of the bone-repair composite to mimic the mammalian bone. The bending modulus of the bone-repair composite is at least 3 GPa, wherein the bending modulus of the bone-repair composite is similar to a cortical bone. The core of the bone-repair composite is coated with a low temperature polymer, a co-polymer, a mixture or a blend of polymers, such as a mixture of poly(ε-caprolactone) (PCL) and glyceryl monosterate, or other polymer mixtures with other inorganic or organic materials. The organic materials can include fatty acids, fatty acid salts, hyaluronic acid and small molecules that are similar to those in the extracellular matrix though to be important in the crystallization of HA. The inorganic materials can include sodium chloride, calcium carbonate, and other inorganic compounds. Furthermore, The bone-repair composite can be subjected to a hot compression molding at an elevated temperature, whereby melting the polymers having a lower melting temperature, and thus binding the polymers having a higher melting temperature with the polymers having a lower melting temperature. The bone-repair composite can be subjected to a cold compression molding using a solvent, wherein the solvent is vaporized to melt the sheath, thus binding the sheath to the core, wherein the solvent is selected from a group of solvents, such as toluene, xylene, ethyl acetate, and acetone. The second group of polymers includes a low-temperature melting polymer or a binding polymer. The bone-repair composite is unidirectional or multidirectional. The bone-repair composite further includes filling materials including drugs or bioactive agents, wherein the filling material is used as a binding material or for drug release. The polymer is selected from a group consisting of collagen, hyaluronans, fibrin, chitosan, alginate, silk, polyesters, polyethers, polycarbonates, polyamines, polyamides, co-polymers, poly(L-lactic) acid (PLLA), polyglycolic acid (PGA), poly(D,L-lactide-co-glycolide) (PLGA), and poly(ε-caprolactone) (PCL), and other polymers. The calcium phosphate compound layer is selected from a group consisting of ion-substituted apatite, calcium phosphate, carbonate hydroxyapatite, fluorinated hydroxyapatite, chlorinated hydroxyapatite, silicon-containing hydroxyapatite, tricalcium phosphate, tetracalcium phosphate, monotite, dicalcium phosphate, dicalcium phosphate dihydrate, octocalcium phosphate, calcium phosphate monohydrate, alpha-tricalcium phosphate, beta-tricalcium phosphate, amorphous calcium phosphate, biphasic calcium phosphate, tetracalcium phosphate, calcium deficient hydroxyapatite, precipitated hydroxyapatite, oxyapatite, calcium sulfate, and calcium containing phosphate minerals. The calcium phosphate compound layer is fully or partially aligned to a fiber axis or a polymer crystallites. The calcium phosphate compound layer is anchored to the polymer surface by electrostatic coordinative, or chemical tethering. The bone-repair composite is formed by varying the ratio of the core and the sheath. Other lower melting or processing polymers can be used, as well as the PCL homopolymer by itself, or a PCL copolymer by itself, or a mixture or blend of polymers with other materials.

In accordance with another embodiment of the invention, a method for making a bone repair synthetic composite is provided. The method includes forming an inner core structure with a plurality of a combination of a first set of yarns. An outer sheath structure is formed with a plurality of a combination of a second set of yarns. A secondary structure is formed by braiding an appropriate ratio of the inner core structure to the outer sheath structure to mimic the mechanical strength of a mammalian bone. The first set of yarns being made from a group of polymers, wherein the inner core structure is a first primary structure. The method further includes treating the first set of yarns with a surface modifying chemical, coating the first set of yarns with a mineral layer. The second set of yarns being made from the group of polymers, wherein the outer sheath structure is a second primary structure. The method further includes cutting the inner core structure and the outer sheath structure into a length of a compression mold, arranging the inner core structure and the outer sheath structure into the compression mold, bonding the outer sheath structure to the inner core structure. The method further includes coating the secondary structure with a binding material, drying the coated secondary structure, and compression molding the coated secondary structure at an elevated temperature, wherein the binding material having a lower melting point than the inner core structure and the outer sheath structure. The method further includes coating the secondary structure with PCL, drying the coated secondary structure, and compression molding the coated secondary structure using a vaporized solvent to melt the PCL. The method can further includes the use of elevated temperature in combination of solvent. The use of solvent in a pultrusion process allows the composite to achieve a high calcium phosphate mineral concentration to reach an optimal level of modulus. The inner core structure is formed by assembling a plurality of yarns together; rolling a mesh structure, wherein the mesh structure is knitted, woven, non-woven, braided, stacked, flocked, or felted; or rolling the plurality of yarns and the mesh structure together. A tertiary structure of a desired shape is formed by binding a plurality of the secondary structures or the primary structures with a binding material. The inner core is designed to facilitate water access rate and cellular access rate both longitudinally and laterally, wherein the longitude access is controlled by time, degradation, and/or solubilization of the inner core, wherein the lateral access is controlled by braid density, coating, or binder of the binding material. The surface modifying chemical is alkaline, acidic, oxidizing, ionic or electrostatic. The polymer is selected from a group consisting of collagen, hyaluronans, fibrin, chitosan, alginate, silk, polyester, polyether, polycarbonate, polyamine, polyamide, co-polymer, poly(L-lactic) acid (PLLA), polyglycolic acid (PGA), poly(D,L-lactide-co-glycolide) (PLGA), poly(ε-caprolactone) (PCL), and other polymers. The mineral layer is selected from a group consisting of ion-substituted apatite, calcium phosphate, carbonate hydroxyapatite, fluorinated hydroxyapatite, chlorinated hydroxyapatite, silicon-containing hydroxyapatite, monocalcium phosphate, monocalcium phosphate monohydrate, amorphous calcium phosphate, biphasic calcium phosphate, calcium deficient hydyroxyapatite, oxyapatite, precipitated hydroxyapatite, bone-like apatite, tricalcium phosphate, tetracalcium phosphate, monetite, dicalcium phosphate, dicalcium phosphate dihydrate, octacalcium phosphate, alpha-tricalcium phosphate, beta-tricalcium phosphate, calcium sulfate, and other calcium containing phosphate minerals. The mineral layer is either hydrodynamically aligned/coated or randomly applied onto the polymer fiber by dip or die coating of the polymer fiber using suspension of mineral particles in solvents or polymer solutions. The mineral is coated using an alternating soaking technique, a simulated body fluid technique, supersaturated calcium phosphate solutions, dip coating, sol-gel coating, electrophoresis, electrochemical coating, extrusion coating, pultrusion or brush-on coating methods.

In accordance with yet another embodiment of the present invention, a method for making a calcium phosphate-reinforced composite yarn is provided. The method includes treating an undrawn yarn with a surface modifying chemical. The undrawn yarn is coated with a calcium phosphate solution to form calcium phosphate particles, such that the calcium phosphate particles are anchored on the yarn to form a coated undrawn yarn. The coated undrawn yarn is drawn to form a coated drawn yarn, such that the calcium phosphate particles are orientated in such a way that the calcium phosphate-reinforced composite mimic bone structures. The surface modifying chemical can be alkaline, acidic, oxidizing, ionic or electrostatic. The calcium phosphate particles can be hydrodynamically aligned/coated on the undrawn yarn by dip or die coating of the undrawn yarn using suspension of calcium phosphate particles in solvents or polymer solutions. The calcium phosphate particles can be coated using an alternating soaking technique, a simulated body fluid technique, supersaturated calcium phosphate solutions, dip coating, sol-gel coating, electrophoresis or electrochemical coating, extrusion coating, pultrusion, or brush-on coating methods. The undrawn yarn can be lightly coated or heavily coated. The method further includes applying one or more layers of calcium phosphate to the coated drawn yarn, treating the coated drawn yarn with bone growth enhancing agent. The calcium phosphate solution can be in the form of a slurry, where the precipitated calcium phosphate compound is coated on the undrawn yarn.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIGS. 8A to 8C are schematic illustrations of the mechanism, respectively, before, during, and after nucleation and growth of CaP on a hydrolyzed polyester yarn surface according to an embodiment of the invention.

FIG. 9 depicts tensile stress-strain curves of the composites fabricated at various conditions according to an embodiment of the invention.

FIGS. 15A and 15B depict a comparison of the alkaline-treated undrawn PLLA yarns with drawing (FIG. 15A) and without drawing (FIG. 15B) after biomimetic coating with hydroxyapatite.

FIGS. 16A to 16H are schematic views of the steps in the fabrication of the novel composite according to an embodiment of the invention.

FIGS. 17A, 17AA, 17B, and 17C depict various levels of detail in a composite construction according to one embodiment of the invention.

FIG. 18 depicts the Young's modulus and flexual strength of pure PCL, PCL-PLLA, and PCL-HA-PLLA.

FIG. 23 is a flowchart of a design for fabrication of composites according to an embodiment of the invention.

FIGS. 24A, 24AA, 24B, 24BB, 24C, 24CC, 24D, and 24DD depict various composite constructions according to four embodiments of the invention.

DETAILED DESCRIPTION

Cyclic Precipitation Technique

Figure 1:
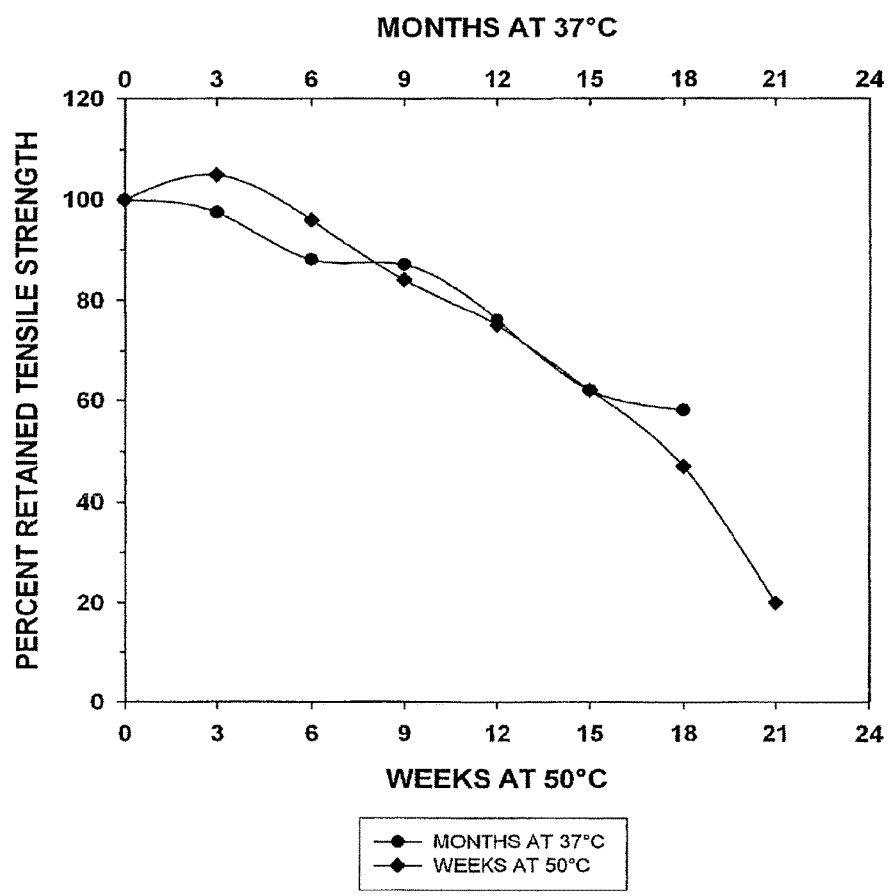
FIG. 1 is a chart showing comparative percent retained tensile strength for PLLA suture in pH 7.4 buffer solution at 37° C. and 50° C.

The invention will now be described with reference to the drawing figures, in which like reference numerals refer to like parts throughout. An embodiment in accordance with the present invention provides a method for making a bone repair synthetic composite with calcium phosphate and absorbable fibrous materials. After a few coating cycles, a desired amount of calcium phosphate is coated onto the fibrous materials. The fibrous materials are then assembled into a unidirectional composite using a poly(ε-caprolactone) matrix. Furthermore, growth factors may be incorporated within the absorbable fibrous materials, such that the release of the growth factors may be controlled through the various degradation rates of the fibrous materials.

Introduction

Natural bone is a complex hierarchical structure of mineralized collagen consisting of an orderly deposition of hydroxyapatite $[Ca_{10}(PO_4)_6(OH)_2]$ (calcium phosphate) within a type I collagen matrix. Recent efforts for fabricating new functional biomaterials involved mimicking these hierarchical structures, albeit using complex chemistry and tedious procedures. Calcium phosphates, mainly as a hydroxyapatite coating on polymer surfaces, not only enhance tissue compatibility, but also can be deployed as hard-tissue generation matrix.

As used herein, the term "calcium compound," "calcium phosphate compound," "calcium phosphate mineral compound" or "calcium phosphate" can be minerals or substances which can include some combination or compound including a form of calcium phosphate, including, but not limited to, ion-substituted apatite, calcium phosphate, carbonate hydroxyapatite, fluorinated hydroxyapatite, chlorinated hydroxyapatite, silicon-containing hydroxyapatite, monocalcium phosphate, monocalcium phosphate monohydrate, amorphous calcium phosphate, biphasic calcium phosphate, calcium deficient hydyroxyapatite, oxyapatite, precipitated hydroxyapatite, bone-like apatite, tricalcium phosphate, tetracalcium phosphate, monetite, dicalcium phosphate, dicalcium phosphate dihydrate, octacalcium phosphate, alpha-tricalcium phosphate, beta-tricalcium phosphate, calcium sulfate, or other calcium containing phosphate minerals.

Poly-L-lactic acid (PLLA) yarn is prepared by melt extrusion of thoroughly dried PLLA resin. The yarn can be produced in a range of deniers by varying the number of filaments and the denier per filament. In a typical extrusion at a spinning temperature of about 240° C., undrawn 30 filament PLLA is collected on a bobbin then drawn about five times its original length with heat in the range of about 100 to 110° C. to give 120 denier yarn with a tensile strength in the range of about 3.8 to 4.2 grams per denier. The drawing can be done in either one or more stages.

The PLLA yarn can be used to fabricate composites either directly with minimal strength enhancing steps or indirectly through a braided suture structure that might involve annealing or hot-stretching to enhance strength and resorption characteristics. Yarns can be processed as is on skeins or after plying and overbraiding with a small sheath to keep the yarn in place but not interfere with coating steps. As one example, forty ends of 135 denier yarn is plied together and used as a core in an eight carrier braider with two bobbins of 120 denier PLLA yarn and a gear ration of 82/72 to obtain a braid with about 4 to 5 picks per inch.

PLLA fiber provides a retained strength profile that is well suited for orthopedic applications. Fully processed PLLA suture will retain about 50 to 60% of its original tensile strength after eighteen months at 37° C. in buffer solution. In accelerated in vitro testing at 50° C. it has been found that one week at 50° C. corresponds to about one month at 37° C. (see FIG. 1). When unprocessed PLLA yarn is tested at 50° C. (see FIG. 2) it retains about 50 to 60% of its initial strength at eight weeks which corresponds to about eight months at 37° C. Thus, depending on the processing of the PLLA yarn there is a range of about eight to eighteen months that will be needed for the PLLA to retain 50 to 60% of its original tensile strength.

A key step in the fabrication of these composites is the nucleation and growth of CaP on the supporting polymer matrix. A biomimetic deposition process was developed wherein the polymer substrates were soaked in simulated body fluid (SBF). SBF contains ions such as $Na^+$, $K^+$, $Ca^{2+}$ or $Mg^{2+}$ with concentration and pH similar to that of human blood plasma. Contact of SBF with a surface can lead to the formation of calcium phosphate on the surface. Other coating methods, such as plasma spray and co-precipitation can also be used. However, an inherent drawback of the biomimetic coating method using SBF is the amount of time required to deposit a large quantity of calcium phosphate (normally a few days to a few weeks), because the driving force for precipitation is small.

In the present invention, to achieve high modulus composites, polymer fibers were coated with CaP utilizing a cyclic-soaking technique, which permits controlled fabrication of composites with higher mechanical properties. A cyclic soaking technique was used for the nucleation and growth mechanism of CaP on poly(lactic acid) (PLA) fibers at room temperature. The deposition of CaP on the polymer surface was characterized using gravimetric measurements and environmental scanning electron microscopy (ESEM) images. These results are crucial for understanding the possible mechanism of mineralization in tissues in general, and fabrication of high-modulus composites for tissue engineering applications in particular.

EXAMPLE

CaP Coating on Fully Drawn PLA Yarn

Commercially available poly-lactic acid (PLA) yarn ($M_w$~121 kDa, $T_g$~55° C., $T_m$~175° C.) was obtained from Teleflex Medical Incorporated. Each yarn contained about 30 filaments, with the filaments having an average diameter of 24.5 μm. The PLA yarn was wound around a rectangular, using a custom-built winding machine that allowed for the control of winding speed and tension. During this stage, care was taken to avoid overlapping of the yarn on the frame. A linear spinning rate of 20 cm/min and a tension of approximately 6 N were used for all the experiments. The yarn was then soaked in 1 N NaOH for 1 min. at 25° C. to saponify the surfaces of fibers. The soaked yarn was rinsed in distilled water and air-dried.

The saponification process was checked in several ways. In one test, water contact angles of the treated PLA films were measured by the sessile drop technique (advancing angles) using a contact angle measurement apparatus (Rame-hart Model 100, USA). To fabricate the films, PLA yarn was dissolved in chloroform and solvent cast at room temperature to obtain a thin film which was hot-pressed (Model 2731, Carver Laboratory Press, USA) at 150° C. for about 2 min. under a hydraulic pressure of 100 MPa to remove any bubbles formed during solvent casting. The PLA film thus obtained was cut into 1 $cm^2$ pieces and treated with 1 N NaOH for 1 min at room temperature. The treated films were rinsed twice in distilled water and dried. A 5-μL water drop was placed on the surface of each PLA film (NaOH treated and untreated), and the contact angle was measured to determine the wettability of the specimen. All measurements were recorded at room temperature and each test was repeated five times on different films.

CaP was deposited on the hydrolyzed PLA yarn using a cyclic soaking technique as follows: 100 mL of calcium nitrate (99% pure, Sigma) and 164 mL of ammonium orthophosphate (99% pure, Sigma) solutions were prepared at a concentration of 1 N, and the pH of each solution was brought up to 12 by adding ammonium hydroxide (Sigma, ACS reagent). The solutions were kept at room temperature while stirring vigorously. The treated yarn was initially soaked in the calcium nitrate solution for a set amount of time from about 0.5 h to about 1 h at room temperature. Then the yarn was washed in distilled water with simultaneous stirring and air-drying. The stirring rate during washing was varied between 80-800 rpm for 0.5 or 1 h to determine its effect on the amount and quality of CaP deposited on the yarn. The dried yarn was soaked in ammonium phosphate solution for the same amount of time, washed and dried in the same fashion as that for calcium nitrate solution. The amount of CaP deposited on the yarn was measured gravimetrically after each cycle. This cyclic soaking process was repeated six times, beyond which the deposited CaP was observed to detach from the PLA yarn. Fresh solutions of calcium nitrate and ammonium phosphate were used for each cycle, to avoid the deposition of CaP particles suspended in the used solutions.

Composite Preparation

To prepare the composites, the CaP-coated yarn was coated with 2 vol % PCL (MW=43 kDa) solution and air-dried overnight in a vacuum to remove excess solvent. A Carver Laboratory Press (Model 2731, USA) was used for compression molding of composites. Initially, the parallel platens in the hot-press were heated to about 55° C. and maintained for about 30 min. A custom-made, three-piece aluminum rectangular mold containing six slots each of 4 cm×0.5 cm×0.5 cm dimensions was stacked with PLA yarn coated with CaP and PCL and held at 55° C. for about 2 min. under a hydraulic pressure of about 150 MPa. Finally, the mold was cooled to room temperature under the same pressure and the specimens were detached from the mold. Typically, specimens prepared using this mold had dimensions of 4 cm×0.5 cm×0.2 cm with the specimen thickness varying slightly for different types of composites.

CaP Coating on PLA Film

Poly(lactic acid) yarn dissolved in chloroform was solvent-cast at room temperature and hot-pressed at about 150° C. for about 2 min. to obtain a smooth film of 0.5-mm thickness. The PLA film was hydrolyzed in 1 N NaOH for 1 min, washed multiple times in distilled water and air-dried. CaP was deposited on the hydrolyzed PLA film using the same cyclic-soaking technique as employed for PLA yarn.

Characterization of the PLA Yarn and PLA Film

The gold-coated surfaces of the as-received PLA yarn, as-pressed PLA film, PLA yarn and film after hydrolysis and after each cycle of biomineralization were observed using an environmental scanning electron microscope (Philips ESEM 2020) operating at 20 kV. An X-ray diffractometer (Brüker AXS D 5005) with a Ni-filtered Cu—$K_\alpha$ radiation was used for the X-ray defraction (XRD) measurements after the CaP powder was isolated by dissolving the CaP-coated yarn in tetrahydrofuran (THF) and repeatedly washing the residuals with ethanol. Data was collected using a scan speed of 1.0°/min and a scan step of 0.02°.

Mechanical Testing of Composites

A three-point bending test (ASTM D790) was used to measure the flexural modulus and flexural strength at break of the fabricated composites. An Instron test machine (1011 Instron Instruments, UK) with a 50-N load cell was employed with a cross-head speed of 1 mm/min. The ratio of length to thickness of the specimen was 16. The flexural stress and strain were calculated from the load and deflection data collected on a data acquisition system. Six specimens were tested for each type of composite (explained in Table 2) with a three-level full-factorial experimental design with no repetitions.

Results and Discussion

Hydrolysis of PLA Yarn

Figures 3A, 3B:
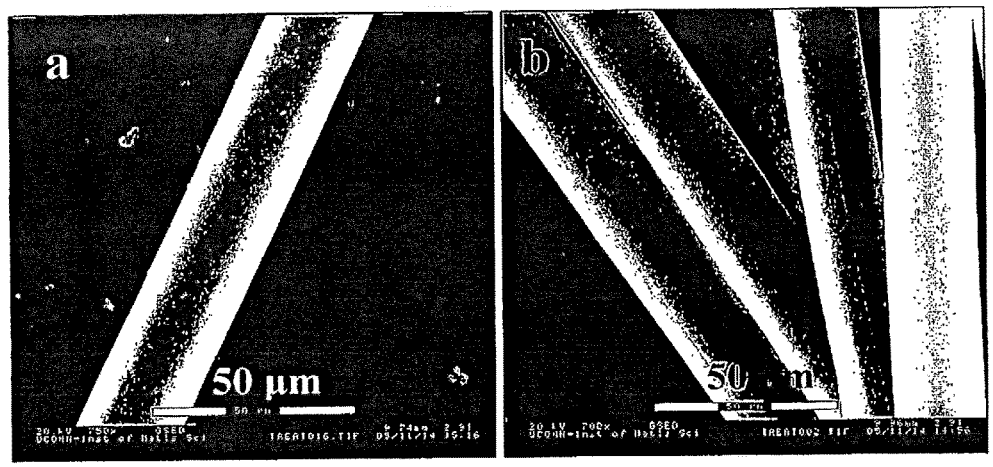
FIGS. 3A and 3B, respectively, depict PLA yarns before hydrolysis and after hydrolysis with 1 N NaOH for 1 min according to an embodiment of the invention.

Surface hydrolysis of the PLA yarn was achieved by soaking the as-obtained yarn in an aqueous solution of 1 N NaOH for 1 min. The hydroxide anions in the solution are expected to hydrolyze the ester groups on the surface of the yarn, resulting in the breakage of polymer chain and the formation of —COO⁻ and —OH groups on the termini of the two new chains. FIGS. 3A and 3B show PLA yarn before and after treatment, respectively. While the PLA yarn remained intact during hydrolysis, the average fiber diameter decreased slightly from 24.58±0.82 to 23.59±0.57 μm (t=3.44 and p=0.002) and the surface of individual fibers appeared slightly rougher [FIG. 3B]. The observed decrease in the diameter of the polyester yarn was likely due to hydrolysis at multiple points on the polymer chains near the surface, reducing the polymer to smaller fragments which were soluble in the solution. Surface hydrolysis of polyesters is known to result in enhanced hydrophilicity, indicative of an increase in the amount of carboxylic acid and hydroxyl groups on the surface, which corresponds to the reduction in contact angle from 81.6° to 75.4° for the NaOH-treated PLA films. Previous studies have shown that carboxylic acid groups can promote the nucleation of CaP on substrates. Moreover, due to its higher surface energy, rougher surfaces might facilitate rapid growth of CaP compared to the smooth surfaces. Though higher concentration of NaOH or higher soaking time contributes to further increase of surface functionalization, it might result in faster degradation or bulk hydrolysis of PLA yarn.

CaP Coating on PLA Yarn

Figure 4:
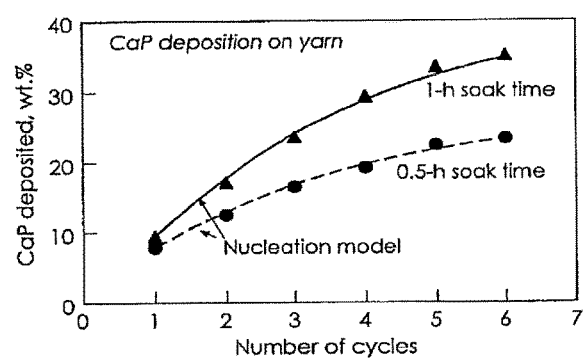
FIG. 4 depicts the amount of CaP deposited on a yarn with increasing repetition cycles and increasing deposition time.

Using a cyclic soaking technique at room temperature, the net amount of CaP deposition was found to increase with soaking repetitions as well as with soaking time for each repetition. As shown in FIG. 4, the amount of deposited CaP increased with soak time. The amount of CaP deposited for 1-h soak time was larger than that for 0.5-h soak time at all repetitions. Gravimetric analysis indicated that around 35 wt % of CaP was deposited after 6 cycles each at 1-h soaking time.

In a similar study involving the calcium phosphate deposition on chitosan using a cyclic soaking method, 57 wt % of calcium phosphate was deposited after 15 repetitive cycles of 15 min each. There was also a decrease in the amount of CaP retained on PLA yarn with increasing stirring rate (p=0.005) during the washing of yarn in distilled water. Table 1 illustrates the decrease in the net amount of CaP deposited after a first repetition cycle with increasing stirring rate from 100 to 800 rpm and with increasing stirring time during washing of coated yarn in distilled water.

TABLE 1

| | Wt % of CaP deposited | | | |
|---|---|---|---|---|
| | 0.5-h stirring time | | 1-h stirring time | |
| Stirring rate, rpm | 0.5-h deposition time | 1-h deposition time | 0.5-h deposition time | 1-h deposition time |
| 100 | 8.14 | 9.21 | 7.62 | 9.71 |
| 300 | 7.59 | 8.85 | 7.22 | 9.1 |
| 500 | 7.1 | 8.07 | 7.01 | 8.66 |
| 800 | 6.77 | 7.9 | 6.84 | 8.15 |

Table 2 details the amount of CaP deposited on the yarn with increasing number of cycles and soaking time for each cycle. Even higher number of cycles resulted in the detachment of CaP from the yarn.

TABLE 2

| | wt % CaP deposition | | Flexural modulus, GPa | |
|---|---|---|---|---|
| Repetition cycles | 0.5-h soak time | 1-h soak time | 0.5-h soak time | 1-h soak time |
| 1 | 7.8 | 9.45 | — | — |
| 2 | 12.4 | 17.4 | — | — |
| 3 | 16.5 | 23.7 | — | — |
| 4 | 19.2 | 29.4 | — | — |
| 5 | 22.4 | 33.6 | 3.94 | 4.66 |
| 6 | 23.3 | 35.1 | 6.45 | 7.89 |

A consistent increase of modulus with increasing CaP content in the composites was observed (Table 2). A flexural modulus as high as 7.9 GPa was achieved for the composites prepared under the conditions of 1 h soaking at each step and after 6 soaking cycles. This value of modulus falls into the lower end of the elastic modulus of human cortical bone, 3-30 GPa. The toughness of the composite can be measured using a three-point bending test to find out the energy required to fracture the composite. None of the composites broke in a brittle fashion during the bending test, indicating that the composites not only had a high modulus, but also superior toughness. The toughness of the composite can be measured as the area under the stress-strain curve, having a unit of joules per cubic meter. The composite's shape, thickness, and size and the testing speed can be varied when applying the three-point bending test. Furthermore, the tension test can also be used to test the toughness of the composite. Annex A1 of ASTM D 882 provides a description for the tension test.

Figure 5A:
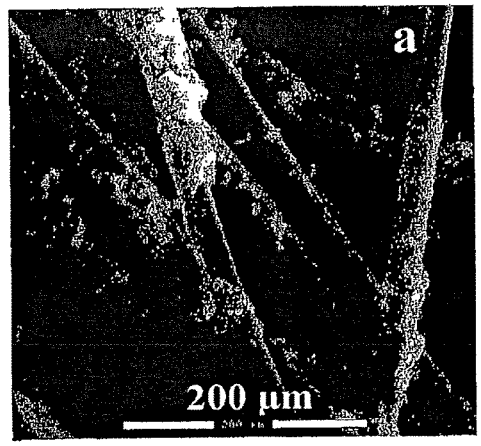
FIGS. 5A to 5D depict ESEM images showing CaP deposition process on PLA yarn after (FIG. 5A) first (FIG. 5B) third (FIG. 5C) fifth and (FIG. 5D) sixth cycles using a cyclic soaking technique according to an embodiment of the invention.
Figure 5B:
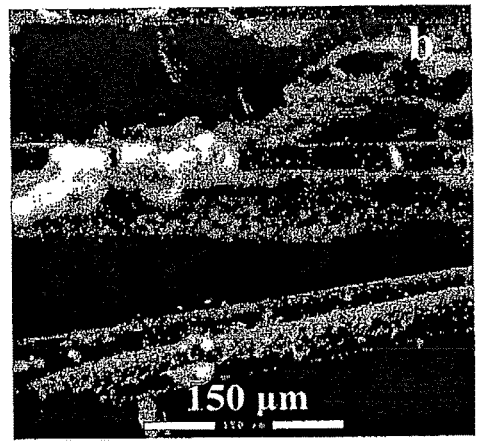
Figure 5C:
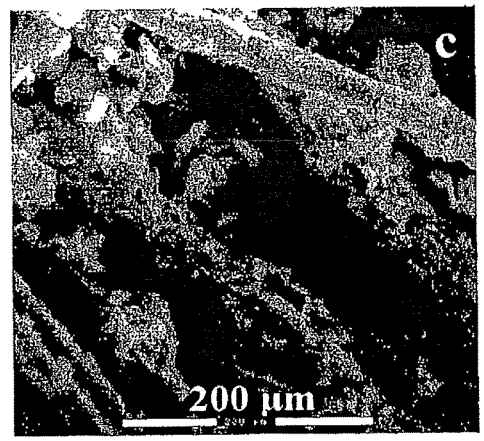
Figure 5D:
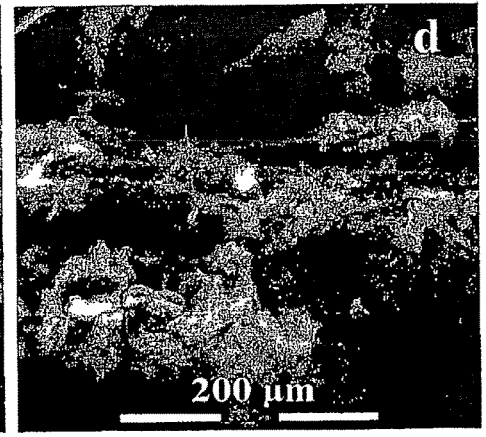

The macroscopic structure of the CaP deposited on the PLA yarn obtained from 1-h deposition time cycles was analyzed by ESEM. Compared to the plain hydrolyzed yarn shown in FIG. 3B, heterogeneous nuclei of CaP can be seen clearly on the surface of the yarn as shown in FIG. 5A. As the repetition cycles increased, the deposition on the fibers increased and the morphology of the yarn changed progressively as shown in FIGS. 5A-5D. These findings are in qualitative agreement with the gravimetric analysis of the deposit on the yarn. From the images in FIGS. 5A-5D, it can be observed that the CaP was not coated uniformly on the entire surface of the yarn after first cycle. Rather, heterogeneous CaP deposits were observed in the ESEM images taken randomly over the entire surface of the hydrolyzed yarn. However, during subsequent cycles, these deposits grew to cover additional surfaces of the yarn. After the fifth and sixth cycles, the yarn surface was completely covered with large amounts of CaP. The carboxylate groups along the surface of the treated yarn should provide favorable sites for $Ca^{2+}$ ions to bond to the substrate, thereby providing a site for the formation of CaP nuclei.

Figure 6:
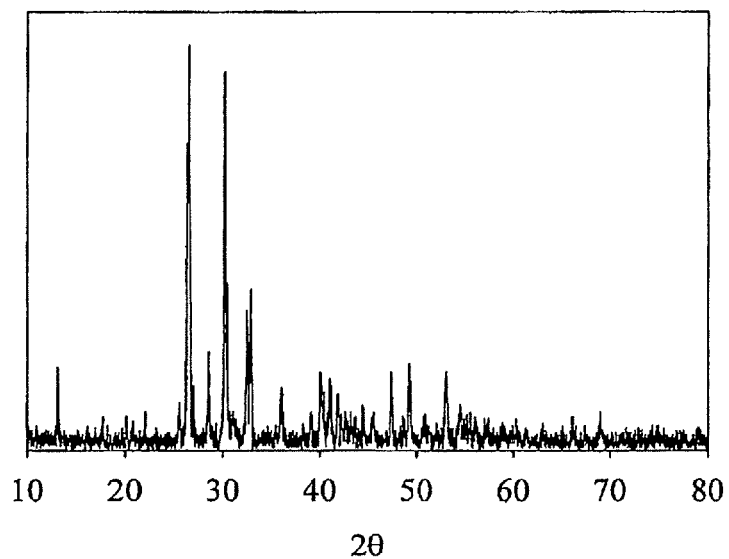
FIG. 6 depicts an XRD pattern of monetite ($CaHPO_4$) deposited after a sixth cycle according to an embodiment of the invention.

The CaP phase deposited on the PLA yarn as judged from the XRD pattern shown in FIG. 6 was observed to be monetite ($CaHPO_4$). Multiple peaks that could be assigned to monetite were detected around $2\theta=26°$, $32°$ and $40°$. The peaks at $2\theta=26°$, $31°$, $32°$ and $33°$ were assigned to the (002), (211), (112) and (300) diffractions of monetite, respectively. Earlier investigations suggest that monetite is bioactive and can be used as bone-inducing mineral.

CaP Coating on PLA Film Using a Cyclic Soaking Method

Figure 7A:
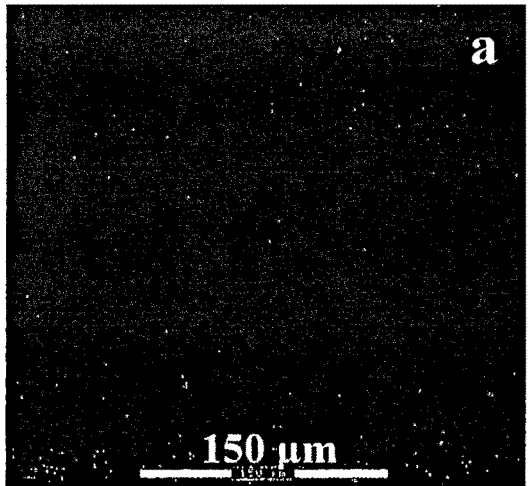
FIGS. 7A to 7E depict ESEM images of the PLA film subjected to, respectively, an increasing number of cyclic soaking processes according to an embodiment of the invention.
Figure 7B:
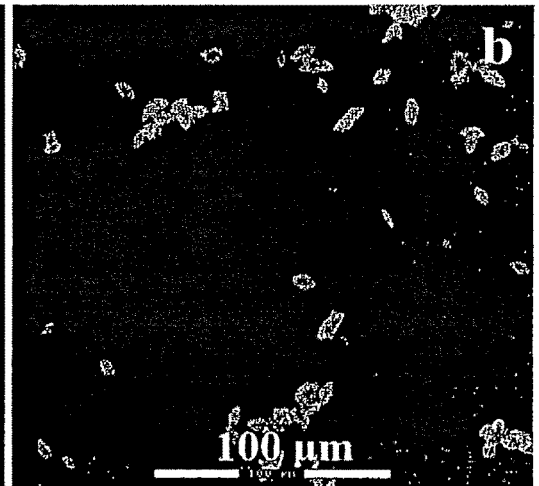
Figure 7C:
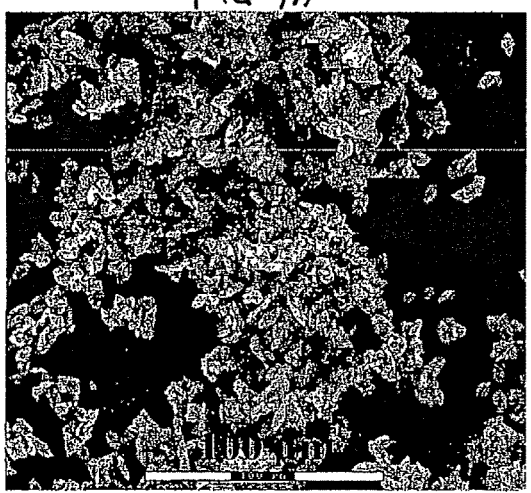
Figure 7D:
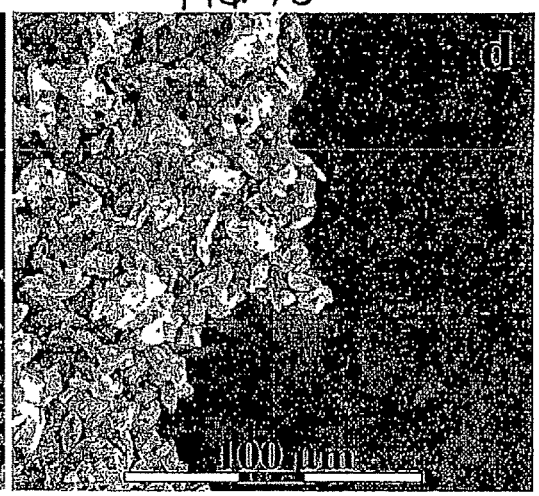
Figure 7E:
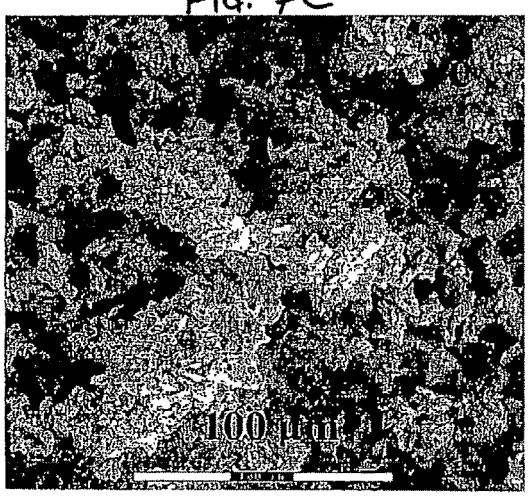

To elucidate the observed phenomenon of CaP formation on the hydrolyzed polyester yarn via heterogeneous nucleation and growth process, CaP coating was done on the hydrolyzed PLA film surface using the same cyclic soaking procedure. The non-hydrolyzed film subjected to cyclic soaking treatment exhibited no signs of nucleation, while the hydrolyzed film (FIG. 7A) demonstrated the nucleation of CaP after first cycle (FIG. 7B). During the second, third and fourth cycles, the CaP grew rapidly from the initial deposits, though the surface of the film in the background can be clearly seen. FIG. 7D represents the film which was partially hydrolyzed and coated with calcium phosphate and the distinction between the coated and the non-coated areas can be clearly seen. The CaP grown on PLA film displayed a thin, platelet-like crystalline morphology as shown in FIG. 7E similar to the calcium phosphate deposited via the biomimetic process using SBF.

During the initial stages of nucleation, the interaction between $Ca^{2+}$ and carboxyl groups on hydrolyzed polyester surface might lead to the formation of a complex such as —$COO^-Ca^+$—$NO_3^-$ or —$(COO)_2Ca^{2+}$ through ion exchange. During soaking in ammonium phosphate solution, it is expected that phosphate ions will interact with the calcium ions on the yarn surface, as shown in FIGS. 8A-8C.

FIGS. 8A-8C are schematic illustrations of the mechanism of nucleation and growth of CaP on the hydrolyzed polyester yarn surface according to an embodiment of the invention. In FIG. 8A, hydrolysis of polyester surface exposed the carboxyl groups on the surface containing sodium ions. In FIG. 8B, during the first soaking cycle in calcium nitrate solution, $Na^+$ ions are replaced with $Ca^{2+}$ ions leading to the formation of —$(COO)_2Ca$, with —$COOCa^+NO_3^-$ as by-product (not shown). FIG. 8C depicts the formation of bonds between $HPO_4^{2-}$ and $Ca^{2+}$ during the first soaking cycle.

An analysis of the nuclei formation and growth thereafter is essential in understanding the CaP forming conditions on the polymer substrate. Since the substrate was washed after each soaking cycle, formation of nuclei in the solution can be ruled out. It is generally believed that heterogeneous nucleation is dominant at low supersaturations. Moreover, heterogeneous nucleation is kinetically and thermodynamically favorable as the interaction between a growing nucleus and a substrate surface represents a lower net interfacial energy than a small nucleus in the surrounding solution. This indicates that the initial calcium binding to the substrate may govern the deposition process during the initial stages. The overall reaction occurring during the precipitation of monetite from these aqueous solutions can be written as:

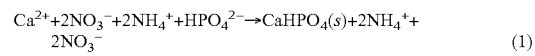

$$Ca^{2+}+2NO_3^-+2NH_4^++HPO_4^{2-} \rightarrow CaHPO_4(s)+2NH_4^+ + 2NO_3^- \quad (1)$$

These results can be compared to the reports involving biomineralization of CaP on polymers by soaking the substrate in SBF for prolonged period of time to deposit the mineral. The induction period for the nucleation of calcium phosphate on polymer substrates in SBF was almost 24 h, independent of the kind of organic polymer. Calcium phosphate deposition was initiated by the nucleation of calcium phosphate induced by dissolved silicate and calcium ions arising from the bioactive glass. In a similar study involving calcium phosphate deposition on silk fibers using SBF route, the authors reported that the functionalized silk surface took 7 days to induce minimal amount of calcium phosphate in SBF, while the non-functionalized silk surface didn't show any signs of deposition even after 7 days. In all the above studies, CaP with bone mineral composition and structure (i.e., hydroxyapatite) was produced in SBF. However, the deposition of CaP on the substrate took much more time compared to the cyclic soaking technique.

Mechanical Properties of the Composites

Figure 10A:
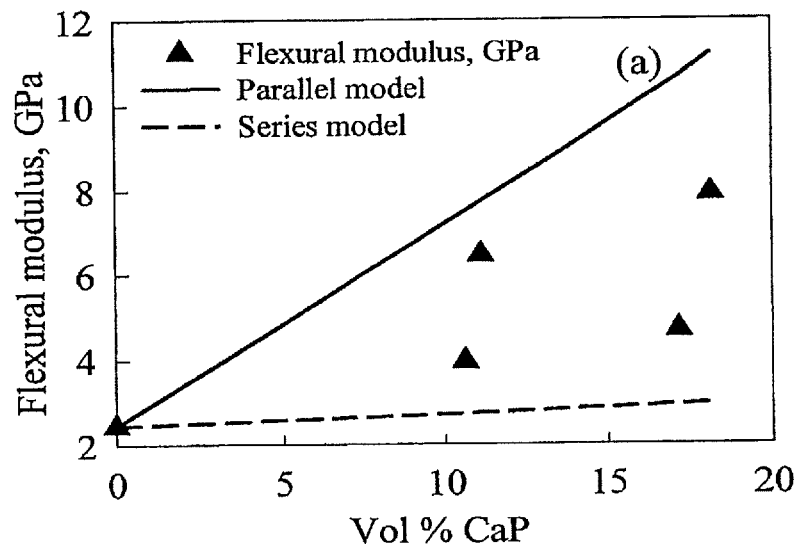
FIGS. 10A and 10B depict the mechanical testing results for flexural properties of the composites prepared at various conditions according to an embodiment of the present invention.
Figure 10B:
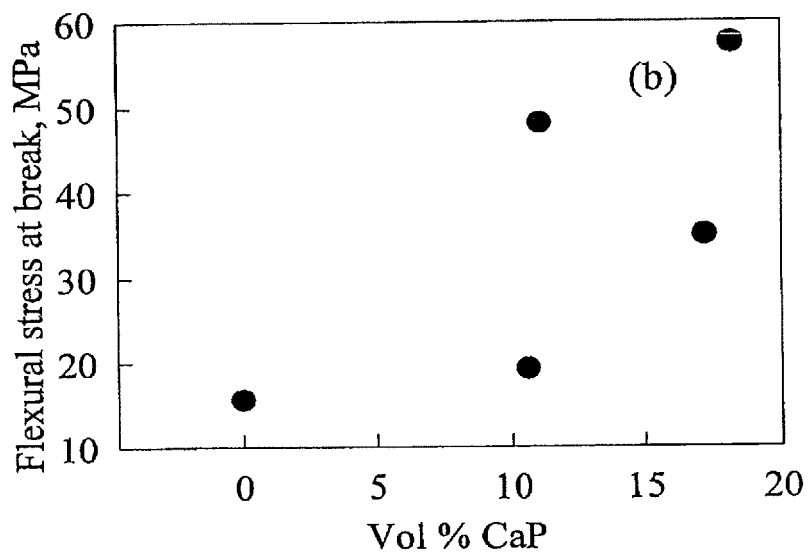

FIG. 9 depicts tensile stress-strain curves of the composites fabricated at various conditions. The flexural properties of the composites are shown in FIG. 10. When the mechanical properties of the PLA-PCL-CaP composites were compared to those of constituent polymers with no CaP loading, significantly higher modulus values were observed, which demonstrates the indirect effect of deposition time and repetition cycles in improving the modulus multifold. Table 2 describes the notation used for the composites prepared at various soaking times and cycles. The composites prepared with 1-h soaking time and 6 repetitions (1-h-6×) exhibited a modulus value of 7.9 GPa while those prepared with 0.5-h soaking time and 5 repetitions (0.5-h-5×) showed 3.9 GPa. Nevertheless, all the composites tested in this study demonstrated modulus values in the range 2.4-7.9 GPa, which are at the lower end of the 3-30 GPa range of the bending modulus of human physiologic bone.

In general, the rule of mixtures provides the simplest method for the estimation of the mechanical properties of the composites in terms of its constituents. For the elastic modulus, the parallel model based on iso-strain and the series model based on the iso-stress assumptions have been usually employed. The parallel model (Eq. 2) provides the upper-limit value of the modulus $E_p$, while the series model (Eq. 3) gives the lower-limit $E_s$. The equations are:

$$E_p = \phi E_f + (1-\phi)E_m \quad (2)$$

$$E_s = [\phi/E_f + (1-\phi)/E_m]^{-1} \quad (3)$$

where $\phi$ is the volume fraction of the filler in the composite and $E_f$ and $E_m$ are the moduli of filler and matrix in the composite, respectively. The predicted modulus values from the models were calculated taking into account the modulus of pure PLA-PCL composite with no filler (2.45 GPa as observed for the PLA-PCL composite in this study) as $E_m$ and the modulus of CaP (50 GPa) as $E_f$, density of PLA-PCL as 1.3 and density of CaP as 3.16. As expected, the moduli of the composites observed in this study fall within the upper and lower bounds calculated using the parallel and series models.

In addition, the bending moduli and flexural strength at yield of the composites tested in the present study are significantly higher than the values reported in literature for PLA-CaP composites. An important factor contributing for the observed increase in the bending yield strength of these composites, compared to the conventional PLA-CaP composites, is the unidirectional alignment of PLA yarn coupled with the CaP particles surrounding them. It can be expected that by increasing the CaP content in the composites, higher modulus can be achieved. For example, calculations indicate that modulus values in the range of 10-15 GPa are possible, depending upon the level of each component.

Biomimetic Coating Technique

Calcium Phosphate Coating on Sodium Hydroxide Treated Drawn Yarns

Initially, drawn PLLA yarns are treated with sodium hydroxide. 500 mL sodium hydroxide solution with a chosen molar concentration (0.100-1.00 mol/L) was prepared with sodium hydroxide 1 mol/L solution and de-ionized water at room temperature. Then, a certain amount of drawn PLLA yarns were dipped into prepared sodium hydroxide solution for certain amount of time (2-60 min) at chosen temperature. Next, the treated drawn PLLA yarns were taken out of the sodium hydroxide solution and washed with de-ionized water 3-5 times before being wiped dry and left in the air over night.

After treating the PLLA yarns with sodium hydroxide, layers of calcium phosphate are coated on the PLLA yarns with a biomimetic coating method. First, a SBF solution is prepared by adding sodium chloride, sodium bicarbonate, potassium chloride, potassium hydrogen phosphate, magnesium chloride, 4-(2-hydroxyethyl)-1-piperazineethanesulfonic acid, calcium chloride and sodium sulfate into de-ionized water under sufficient stirring. Then, hydrochloric acid solution was added and the pH value of the solution was adjusted to around 6.0-7.0. Next, sodium hydroxide treated drawn PLLA yarns were dipped into prepared SBF solution and warmed up to certain temperature (40-60° C.) under the biomimetic coating procedure. The treated drawn PLLA yarns were coated with calcium phosphate after 1-6 h and taken out of SBF solution. Then, the coated drawn PLLA yarns were washed with de-ionized water for several times. Lastly, the coated and washed drawn PLLA yarns were air dried overnight.

Calcium Phosphate Coating on Sodium Hydroxide Treated Undrawn PLLA Yarns

Initially, undrawn PLLA yarns were treated with sodium hydroxide. A certain amount of sodium hydroxide solution (20-500 mL) with molar concentration 0.500 mol/L was prepared. Then, a certain amount of undrawn PLLA yarns were dipped into prepared sodium hydroxide solution for 10 min at room temperature. Next, treated undrawn PLLA yarns were taken out of the sodium hydroxide solution and washed with de-ionized water 3-5 times before being wiped dry and air dried over night.

After treating the undrawn PLLA yarns with sodium hydroxide, layers of calcium phosphate are coated on the undrawn PLLA yarns with a biomimetic coating method. First, a SBF solution is prepared by adding sodium chloride, sodium bicarbonate, potassium chloride, potassium hydrogen phosphate, magnesium chloride, an appropriate buffer like HEPES or Tris, calcium chloride and sodium sulfate into de-ionized under sufficient stirring. Then, hydrochloric acid solution was added and the pH value of the solution was adjusted to around 6.0-8.0. Next, sodium hydroxide treated undrawn PLLA yarns were dipped into prepared SBF solution and heated up to certain temperature (40-60° C.). The treated undrawn PLLA yarns were coated with calcium phosphate after 1-4 h and taken out of SBF solution. Then, the coated undrawn PLLA yarns were washed with de-ionized water for several times. Lastly, the coated and washed undrawn PLLA yarns were air dried over night.

Figure 11:
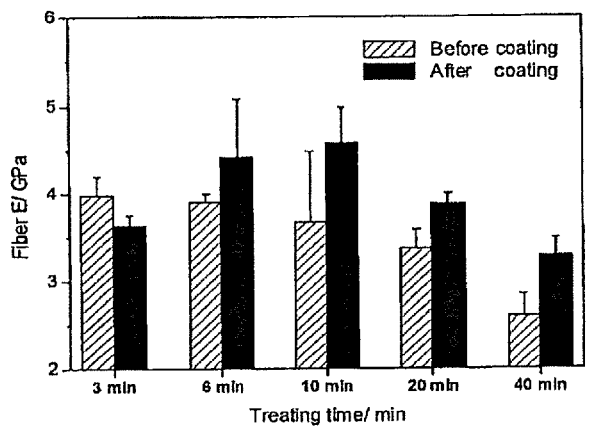
FIG. 11 demonstrates the effect of etching time on the Young's modulus of PLLA drawable single fiber before and after HA coating.
Figure 12:
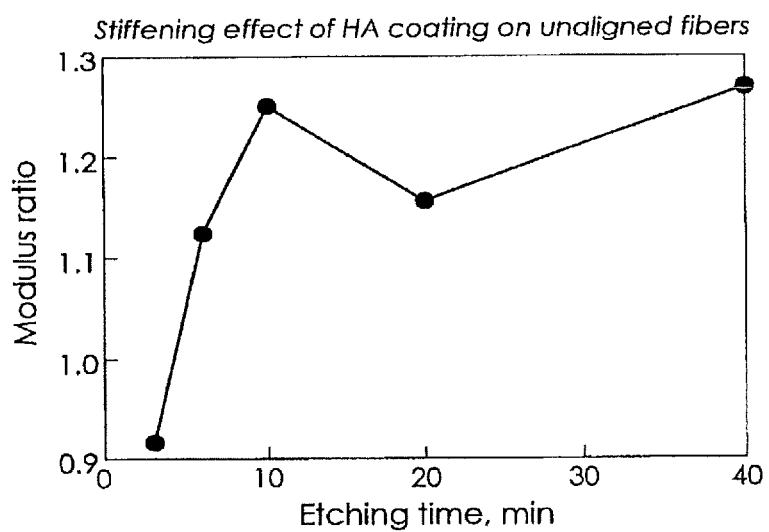
FIG. 12 is a chart showing the stiffening effect of HA coating on unaligned fibers.
Figure 13:
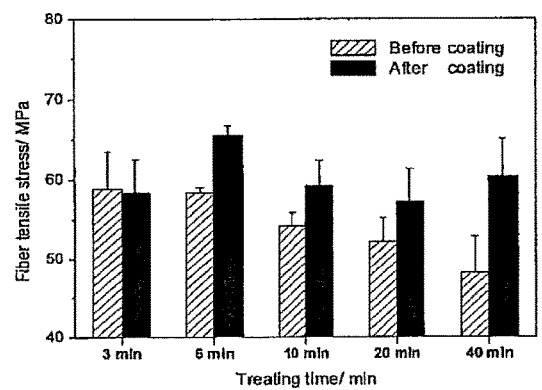
FIG. 13 demonstrates the effect of etching time on the tensile stress of PLLA drawable single fibers before and after HA coating. Treating conditions: [NaClO]=0.05 M, 25.0±0.2° C. Coating conditions: 3×SBF, 60° C., 2 h.

In addition to the etching with sodium hydroxide solutions, the etching process can be carried out in sodium hypochlorite or calcium hydroxide solutions and then similarly coated with biomimetic calcium phosphate. FIGS. 11, 12 and 13 show the effect of treatment time on the Young's modulus of drawable PLLA filament before and after the biomimetic hydroxyapatite coating.

FIG. 11 demonstrates the effect of etching time on the Young's modulus of PLLA drawable single fiber before and after HA coating. The PLLA fibers were etched with [NaClO]=0.05 M, 25.0±0.2° C., and coated at 60° C., 2 h with 3×SBF. FIG. 12 is a chart showing the stiffening effect of HA coating on unaligned fibers. FIG. 13 demonstrates the effect of etching time on the tensile stress of PLLA drawable single fibers before and after HA coating. The PLLA fibers were treated with [NaClO]=0.05 M, 25.0±0.2° C. and coated with 3×SBF, 60° C., 2 h.

In both cases, a minimum etching time of six minutes yields coated filaments with increased values of Young's modulus. The data also shows that if the treatment time is too long the Young's modulus of the uncoated filament is reduced with the increased etching.

Primary Study on Calcium Phosphate Particles' Orientation on Sodium Hydroxide Treated PLLA Yarns A comparison of undrawn PLLA yarns and drawn PLLA yarns were conducted. First, undrawn PLLA yarns with 3-4 cm length were warmed up in water bath to 55-65° C. They were drawn to double length in the water bath, wiped dry and left in the air for 10 min. Next, a 20 mL of sodium hydroxide solution with a molar concentration of 0.500 mol/L were prepared. Then, a same length of undrawn PLLA yarns and newly drawn PLLA yarns were dipped into the prepared sodium hydroxide solution for 10 min at room temperature. The treated PLLA yarns were taken out of the sodium hydroxide solution and washed with de-ionized water 3-5 times before being wiped dry and air dried over night.

Similar to the above stated method, a SBF solution was prepared. Then, the sodium hydroxide treated PLLA yarns were dipped into the prepared SBF solution and heated up to a certain temperature (40-60° C.). Extra SBF solution was also heated up at the same time. The treated PLLA yarns were coated with calcium phosphate after 0.5-1.0 h and taken out of SBF solution.

Next, the PLLA yarns coated after the first cycle (0.5-1.0 h) were drawn in hot water bath (60° C.) again to certain length and put back into extra SBF solution. After being coated with the second cycle (0.5-1.0 h), PLLA yarns were taken out of SBF solution. The coated PLLA yarns were washed with de-ionized water for several times and air dried over night.

Results & Discussion

Figure 14A:
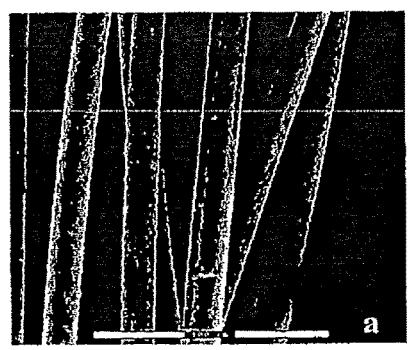
FIGS. 14A and 14B demonstrate alkaline-treated drawn yarn with biomimetic coating at different concentrations of NaOH, respectively.
Figure 14B:
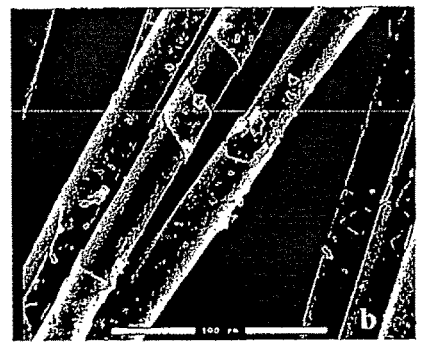

FIGS. 14A and 14B demonstrate alkaline-treated drawn yarn with biomimetic coating. In FIG. 14A, the drawn yarn was treated in 0.5 mol/L of sodium hydroxide for 60 minutes at 70° C. and was then treated with the biomimetic method. A homogenous calcium phosphate coating layer is formed on the surface of the alkaline-treated PLLA yarns using the biomimetic coating process. In comparison, in FIG. 14B, the drawn yarn was treated in 1.0 mol/L of sodium hydroxide for 30 minutes at 25° C. before subjecting the yarn to the biomimetic solution. Unlike FIG. 14A, the calcium phosphate coating layer is not homogenously coated on the drawn yarn. Therefore, the longer soaking time, NaOH concentration, and/or the elevated temperature facilitate the preparation of the drawn yarn for the biomimetic coating.

FIGS. 15A and 15B depict a comparison of the alkaline-treated undrawn PLLA yarns with drawing and without drawing. In FIG. 15A, the alkaline-treated PLLA yarns were not subject to drawing. As shown, calcium phosphate particles were coated on the PLLA yarns. In comparison, in FIG. 15B, the alkaline-treated PLLA yarns were drawn from 2 cm to 4 cm. It is noted that the calcium phosphate particles on the PLLA yarns are aligned and distributed on the drawn yarn. There are numerous benefits on coating the undrawn yarns with calcium phosphate. For example, the surface of the undrawn PLLA yarns can be modified more easily than the fully drawn yarns; thicker and denser calcium phosphate can be formed on these undrawn yarns; increased axial alignment of calcium phosphate coating can be achieved; these coated undrawn yarns can be coated again upon drawing to obtain thicker and denser calcium phosphate coating; and other agents for degradation or enhanced bone growth can be coated upon drawing.

Nucleation Model for CaP Deposition

The simplest picture of deposition of CaP on the yarn is one involving the random nucleation of crystals at equivalent sites that cover the yarn surface. Once the crystal is started, it grows in proportion to the time it is exposed to the solutions.

Definition of variables:
n=number of cycles
$N_A$=density of growing sites
$N_{A0}$=total density of sites
$p_D$=probability of damage per cycle.
$p_N$=probability that a site nucleates a crystal during each cycle
$t_s$=soak time per cycle
w=mass of CaP deposited per active site, per cycle
W=total deposited mass of CaP The chance that one of the $N_{A0}$ possible sites will become active during one cycle is $p_N$. Thus, the rate of change of the number of active sites $N_A$ is given by the probabilistic expression:

$$\frac{dN_A}{dn} = p_N(N_{A0} - N_A) \quad (4)$$

Integration of this expression gives:

$$N_A = N_{A0}(1 - e^{-p_N n}) \quad (5)$$

It is assumed that the deposition rate of CaP is proportional to the number of active sites and the mass per cycle, w, deposited at each active site. The rate for the latter turns out to be a diminishing function of soaking time (see section 3.2) that needs to be determined empirically. It is assumed that $w = \alpha t_s^\beta$, where $\beta < 1$. Reducing the total deposition rate is the chance $p_d$ that the deposit at an active site will be damaged during the rinsing steps that are part of each cycle. For simplicity, it is assumed that it will be removed completely, but the site remains active. Thus, during each cycle, the mass removed will be:

$$N_A p_D W / N_A = p_D W \quad (6)$$

where W is the total mass deposited after n cycles. This expression is equivalent to assuming that the mass of the deposit that breaks will be equal to that of the average deposit. The net rate of CaP deposition will then be:

$$\frac{dW}{dn} = wN_A - p_D W = \alpha t_s^\beta N_{A0}(1 - e^{-p_N n}) - p_D W \quad (7)$$

Figure 2:
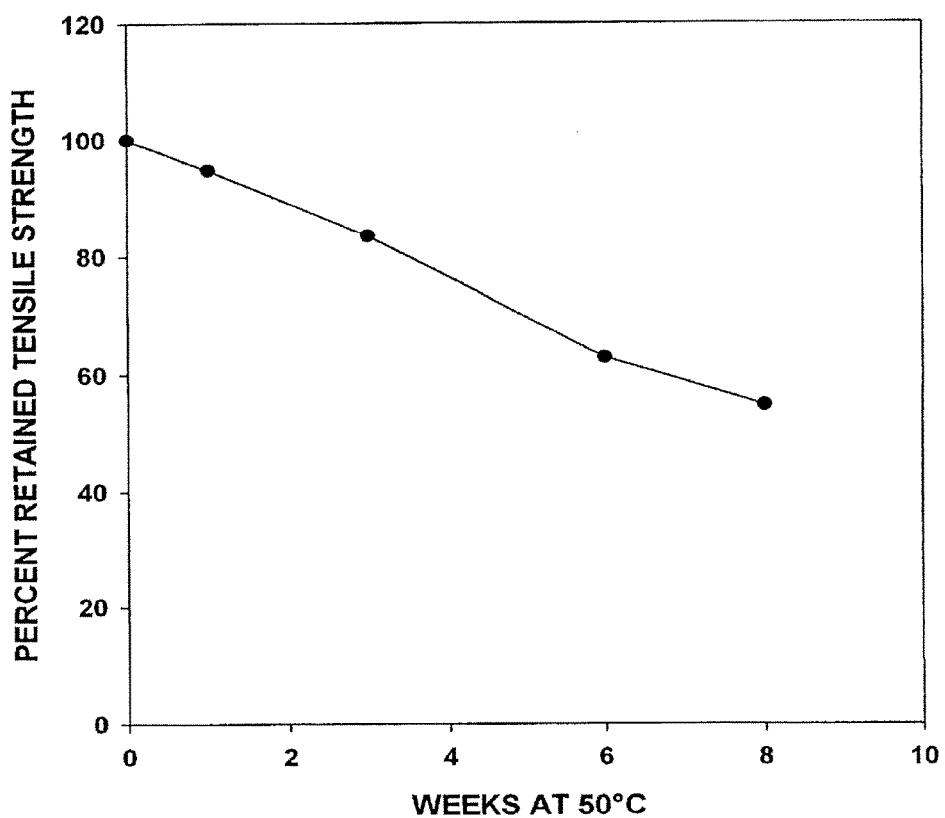
FIG. 2 is a chart showing percent retained tensile strength for PLLA yarn in pH 7.4 buffer solution at 50° C.

The analytical integration of this expression is not readily apparent; thus, it was analyzed in its differential form. After gaining the values of the four parameters $\alpha N_{A0}$, $\beta$, $p_N$ and $p_D$, the equation was integrated numerically with the first observation as the initial value. The results are shown in FIG. 2 as the curves labeled "nucleation model."

As with all analyses of this sort, exclusivity is not proven by a good result. For example, a model involving impinging deposits leading to retarded growth might work as well.

CONCLUSIONS

Monetite was successfully deposited onto the hydrolyzed polyester substrate using a cyclic soaking method from aqueous solutions of calcium nitrate and ammonium phosphate. The amount of CaP formed increased with increasing repetitions and soaking time at each repetition. A heterogeneous nucleation and growth mechanism was proposed to explain the observed phenomena of CaP deposition on the polyester surface. The composites prepared using this technique demonstrated flexural modulus in the range 2.4-7.9 GPa, which are at the lower end of the 3-30 GPa range of the bending modulus of human physiologic bone. Furthermore, it should be possible to fabricate various geometries of porous and bulk scaffolds with CaP using this cyclic soaking route depending on the mold and operating conditions.

Biomimetic coating technique was used on both drawn and undrawn yarns to generate homogeneous calcium phosphate coating. The present invention also demonstrates that the use of a sodium hydroxide under a certain concentration and temperature facilitates the uniform coating of calcium phosphate. Furthermore, the orientation of the coated calcium phosphate particles on the undrawn yarn can change upon drawing.

The yarns were washed with de-ionized water after each coating cycle. Finally, the CaP-coated yarns were coated with poly(ε-caprolactone) solution in tetrahydrofuran (THF), dried, and compression molded at an elevated temperature to form rectangular bars.

Fabrication of Novel Composites for Bone and Delivery of Growth Factors

Introduction

A new bone-repair synthetic composite material, which provides a sustained steady localized controlled release of more than one growth factor and also has sufficient mechanical strength during the bone healing process, is needed. The new material can be described as an calcium phosphate/polymer composite consisting of hydroxyapatite, various thermoplastic binding resins, and a combination of biodegradable polymer fibers, which can be used as separate compartments for delivering different growth factors or delivering the same growth factor with different release rates. The invention provides an effective path for medical-device manufacturers to follow for designing highly functional devices for specific applications, such as long-bone repair, spinal fusion, sternal bone closure, and maxillofacial fixation. Aside from the pursuit of the stated goals, the understanding of polymer-based composite systems will be advanced, as the braiding process provides the opportunity to control precisely the deviation of the composite structure from uniaxiallity and thus the deviation of mechanical properties from those of the ideal uniaxial structure.

Drug Delivery Synthetic Materials

A number of materials have been used as growth factor carriers, including, but not limited to, hydroxyapatite (calcium phosphate), synthetic polymers, demineralized bone, and collagen-based materials.

Most of the polymers used for carriers are biodegradable, and they can be divided into natural polymers and synthetic polymers. Natural polymers include collagen, hyaluronans, fibrin, chitosan, alginate and other animal- or plant-derived polymers. Notably, collagen sponge has become the most commonly specified natural polymer for use as a delivery carrier.

Human bone healing is a relatively slow process, requiring 2-3 months, depending on the patient health conditions and the repair site. Thus, a carrier material with sustained, steady, localized controlled release is required for the human bone healing process. Synthetic polymers, such as poly(L-lactic) acid (PLLA), polyglycolic acid (PGA), poly (D,L-lactide-co-glycolide) (PLGA), polydioxanone (PDO) and poly($\varepsilon$-caprolactone) (PCL), are examples for localized release of growth factors, such as BMP and TGF-$\beta$.

As a biodegradable polymer, semi-crystalline PLLA fiber has been used in sutures, while amorphous PLA copolymers have been used in bone grafts and as drug carriers. One complication in the use of synthetic absorbable polymers like PLA is their degradation by hydrolysis to acidic products, which can accelerate the degradation rate of the polymer and induce local inflammation at the implantation site. However, if it is implanted together with calcium phosphate, the degradation of calcium phosphate forms alkaline products that neutralize the acidic degradation products (lactic acid) of the polymer. Moreover, the degradation rate of the polymer can be tailored to achieve the optimum BMP release rate by altering the polymer molecular weight and/or polymer composition. For example, the degradation rate of 50:50 glycolide-lactide copolymer (PLGA) can be higher than that of PLA. PCL is one semi-crystalline synthetic absorbable polymer that can be processed at low temperatures because of its low cost, extended resorption time and availability at low molecular weight.

Proteins are normally incorporated into polymers at room temperature. BMPs are highly sensitive to thermal processing and some types of chemical exposure, so the major challenge in developing the BMP carrier material is to incorporate sufficient BMP into the structure of the material without compromising the biological activity of the proteins. Unlike most of the ceramics and metals, amorphous polymer materials can often be processed at low temperatures, which make it easy to incorporate proteins into the polymer structure without harming the protein. The release of the protein from the amorphous polymer matrix involves both diffusion of the protein through the matrix and degradation of the matrix polymer. If the protein is incorporated into the structure of the polymer, the protein release rate is largely dependent on the degradation rate of the polymeric matrix, as the diffusivity of one polymer in another is very low. It has been demonstrated that with increasing degradation rate of a lactic acid/lysine copolymer matrix, the release rate of the protein increases.

In Vitro and In Vivo Tests

In vitro studies indicate that growth factors induce cell proliferation, cell differentiation, alkaline phosphotase (ALP) activity, and extracellullar matrix formation. It was also evident that long-term continuous release of growth factors is crucial for bone formation in vitro. Recombinant technology has led to the expressing of human BMPs in quantities suitable for therapeutic applications in pre-clinical animal studies, including mice, rats, rabbits, dogs, sheep, and non-human primates. Bone formation rate can be accelerated due to the presence of BMP. However, faster and more bone healing was observed for the carrier material which provided sustained delivery of the growth factors.

Methodology

Fabrication of Novel Calcium Phosphate/Polymer Composites

A novel composite is fabricated for bone-repair applications using innovative processing techniques. Two approaches are employed to fabricate bar- and sheet-shaped composites, respectively.

The novel process of fabricating the composites is shown schematically in FIGS. 16A to 16H. Different biodegradable polymer fibers 102 (FIG. 16A) are employed to prepare the composites. The polymer fibers 102 are braided into braids 108 (FIG. 16D). These braids can either be coated with hydroxyapatite or non-coated. Some of the polymer fibers 102 are coated with hydroxyapatite using a biomimetic method and then with a thin layer of a low melting polymer to form coated fibers 104 (FIG. 16B, 16C) which is used to form the center core of the braid 118, as shown in FIGS. 17A, 17AA, 17B, and 17C, with uncoated polymer fibers 102 braided in a sheath over it (FIG. 17). Some of the secondary unidirectional structures can then be compression molded (FIG. 16E) to give a rod/bar-shaped composite (FIG. 16F) or used to form a mesh (FIG. 16G, 16H). Furthermore, the uncoated yarn 12 or the coated yarn 104 can also be used to make a mesh without the coating of the low-temperature polymer. The thus-fabricated composites are suitable for varied applications, such as long-bone repair, spinal fusion, sternal bone closure, and maxillofacial fixation. Examples of low melting temperature polymers includes polymers with a melting point below 175° C., semi-crystalline polymers, PCL, polydioxanone, copolymers of PCL with PGA, PDO, TMC or PLA (L or D,L), non-crystalline polymers, PLA-PGA (50:50), poly-D,L-lactic acid, or any polymers having a lower melting temperature than the core structure. The details of the each processing step are described as follows:

EXAMPLES

Composite Components

Two synthetic biodegradable polymer fibers (poly(L-lactic acid) (PLLA) and polyglycolic acid (PGA)), one natural polymer (catgut), one polymer coating (the mixture of poly($\varepsilon$-caprolactone) (PCL) and glyceryl monostearate), and one calcium phosphate coating (mainly hydroxyapatite (calcium phosphate)) are used in construction of the composites. The melting temperature, mechanical properties, and degradation rate of these materials are listed in the following table.

TABLE 3

| Properties | PGA | PLLA | Catgut | PCL | CaP |
|---|---|---|---|---|---|
| Melting temperature, ° C. | 225 | 175 | ~200 | 60 | >1600 |
| Young's Modulus (Gpa) | 7.0 | 6.0-7.0 | 0.1 | 0.4 | 100 |
| Tensile strength (MPa) | 730 | 500-550 | 50-100 | 240 | 40-300 |
| 50% tensile strength loss | 14 days | 18 months | 7 days | 12 months | >2 years |

Nano-CaP Powder Coating 20-30 of the PLLA fibers ($T_m$=175° C.) are formed into yarns. PCL ($T_m$=60° C.) was dissolved in toluene, which is a non-solvent for PLLA. Nano-CaP powders were added to the PCL solution to form a homogenous suspension. The PLLA yarns were then dip coated with the mixture of calcium phosphate and PCL, stacked in a mold, and subjected to compression molding at 60° C. The calcium phosphate load was 25 wt %, and the PLLA to PCL ratio was 6:1. During the compression molding, the PCL melted and acted as a "glue" to bind all the PLLA yarns together. The specimens were then subjected to a three-point bending test, where pure PCL was used as a control.

FIG. 18 shows the flexural strength and Young's modulus of pure PCL, PCL-coated PLLA, and both PCL- and CaP-coated PLLA. The PCL-coated PLLA has much higher strength and Young's modulus than those of pure PCL. With the addition of calcium phosphate in the system, the composite became much stiffer and stronger. Its Young's modulus was at the lower end of that of cortical bone, 3-30 GPa. However, the composite is still too weak to be used at load-bearing applications.

Biomimetic Coating

To mimic the calcium phosphate formation in the biological environment, a biomimetic approach is employed to apply bone-like carbonated calcium phosphate onto the surface of the polymer yarns. The biomimetic coating method produces a calcium phosphate layer on the surface of various biomaterials in simulated body fluid (SBF), which has identical ion concentrations to human blood plasma at body pH (7.4) and temperature (36.5° C.).

In one of the embodiment, a biomimetic method is used to homogenously precipitate nano-calcium phosphate on the surface-modified polymer yarns to achieve a strong calcium phosphate coating. Further, the novel processing technique is employed to co-braid the PCL yarns with PLLA, PGA or PDO yarns. This unique design has the following advantages: (1) instead of using yarns, the braids are bound together using PCL to minimize the PCL to PLLA ratio; (2) it allows to precisely control the amount and the distribution of PLC in the PLLA (or PGA, PDO) fibers; (3) the PCL automatically distributes in a uniform fashion between the fibers when it melts.

The bonding strength between the calcium phosphate coating and a polymer can be improved substantially by pretreatment of the polymer surface with either an alkaline or an acid solution to form polar groups that are confined substantially to the surface of the polymer. It has also been found that calcium phosphate precipitates may align along the fiber axis when carboxylate groups are present on the surface of the uniaxially stretched polymer fibers. As the synthetic polymer yarns used in this study have been prepared through extensive uniaxial stretching during the spinning process, they can be treated with acid or base to render carboxyl or carboxylate binding sites that induces the nucleation of calcium phosphate nano-particles with a preferential orientation. Thus, the yarns are dipped quickly into an acid, a base or a sequential combination of both solutions to attain the necessary surface treatment without modifying the polymer unfavorably. The pretreated yarns are soaked in the SBF solution for various periods, to attain composites with varying calcium phosphate loadings, including no exposure to SBF (zero loading). Such-obtained calcium phosphate precipitations orientate along the polymer fiber axis, which mimics the structure of the aligned calcium phosphate nano-particles on collagen fibrils in natural bone.

The surface properties of the composite before and after soaking in the SBF are thoroughly characterized by a series of techniques, including thin-film-XRD to examine the surface phase distribution, and Fourier transform infra-red (FTIR) to determine the surface functional groups. Surface morphology changes are monitored by scanning electron microscope. The calcium and phosphate ion concentrations in SBF, before and after soaking, are measured by inductively coupled plasma atomic emission spectroscopy (ICP-AES).

Example 1

Drawn PLA fiber yarn (30 filament, 120 denier) was wound around open plastic frames ($2^{1/4} \times 1^{1/8}$ in.). The amount of fiber on each frame varied since the process was done by hand. The fiber and frame were then weighed. The samples were then soaked in simulated body fluid solution (3× concentration) for 12 h to generate a layer of hydroxyapatite (HA) coating on the surface of the PLA fibers. The samples were left to dry overnight. After drying the weight was recorded and was used to calculate the percentage of HA by weight of each sample. The samples were then hot compacted into bars with dimensions around (4×0.5×0.2) cm at a temperature of 175° C. for 30 min. Afterwards, each sample was subjected to a three-point bend test to determine flexural modulus and flexural strength. This was done at a strain rate of 1 mm/min. It is noted that etching is not used in this example. Nonetheless, etching can be used prior to biomimetic coating. Also, a low temperature binding sheath was not used in this example. Instead, the hot compaction was carried out near the melting point of the PLA, at 175° C., thus melting the outer PLA fiber yarns to bind the group of PLA fiber yarns. Calculations were made using the following equations:

$$E_f = \frac{L^3 m}{4bd^3} \quad (8)$$

$$\varepsilon_f = \frac{6Dd}{L^2} \quad (9)$$

$$\sigma_f = \frac{3PL}{2bd^2} \quad (10)$$

Definition of Variables:

P: applied load, N

L: support span, m b: width of the sample, m d: thickness of the sample, m m: slope of the tangent to the initial straight line portion of the load/deflection curve, N/m.

TABLE 4

Flexural Modulus, Strength, and Strain Of Some Self Reinforced PLA/HA Composites.

| Wt % HA | wt % PLA | $E_f$ (GPa) | $\sigma_f^{max}$ (MPa) | $\varepsilon_f^{max}$ % |
|---|---|---|---|---|
| 9 | 91 | 2.2 | 145.9 | 13 |
| 31 | 69 | 3.0 | 29.9 | 7.6 |
| 43 | 57 | 3.4 | 44.0 | 12.1 |

The data obtained from samples containing 9, 31, and 43 wt % HA is shown in Table 4. The data suggest that the flexural modulus increases with HA concentration in spite of the concomitant decrease in PLA content. The data did not show any correlation between HA wt % and flexural strength of the composite. However, the data shows that the flexural strength increases greatly from 44 MPa to 146 MPa when the wt % of PLA fibers was increased. The strain data shows no significant difference between 9 and 43 wt % HA samples but at 31 wt % the maximum strain percent was quite low in comparison to the other samples. Data such as this suggests that a balance should be found between HA and PLA wt % in order to maximize flexural modulus and strength.

Example 2

Direct Coating of Calcium Phosphate Precursors

Pre-formed or calcium phosphate precurors can be directly coated onto PLA fibers. A hydrothermal method is used to make the HA, then the particles are used with PCL to coat over the fibers. In addition, other calcium phosphates can be used.

Figure 19:
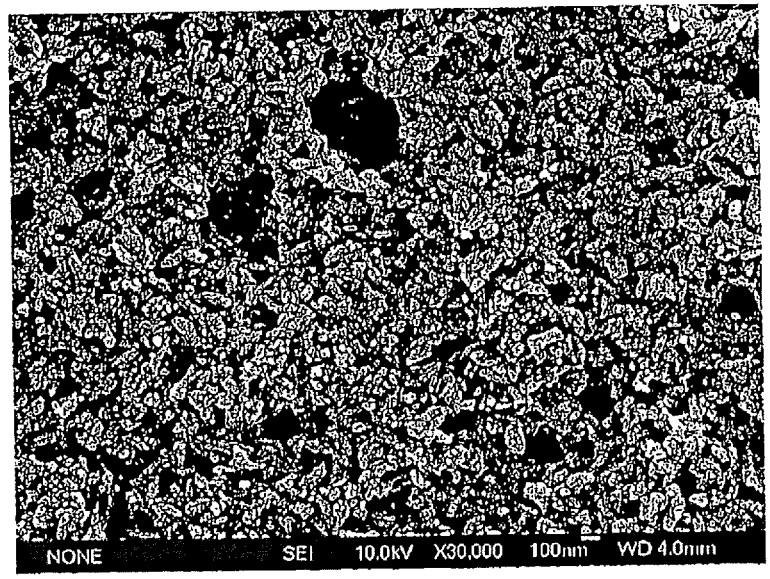
FIG. 19 depicts HA particles used in a bone-repair composite.

The HA particles used in the composite were prepared by reacting of 200 mL calcium nitrate solution (2 g/dL) and 600 mL ammonium phosphate solution (2 g/dL). After drying, the precipitate was ground into powder, which has an average particle size of 120 nm and is shown in FIG. 19. Ten mg of ground HA powder was then added into 10 mL PCL (Dow, MW 80,000) acetone solution (1% wt/wt), which was used to dip-coat the PLA fiber strand composed of 30 fibers with a 22-μm diameter for each fiber. Sixty meters of PCL-HA coated PLA fibers were then aligned and hot-pressed in a 40-mm×5-mm×2-mm mold at 80° C. for 4 min. The resulting composite was taken out after cooling and its composition was PLA:PCL:HA=83:15:2 wt % as determined by TGA. It is noted that etching is not used in this example. Nonetheless, etching is an optional process and can be used prior to biomimetic coating.

Figure 20:
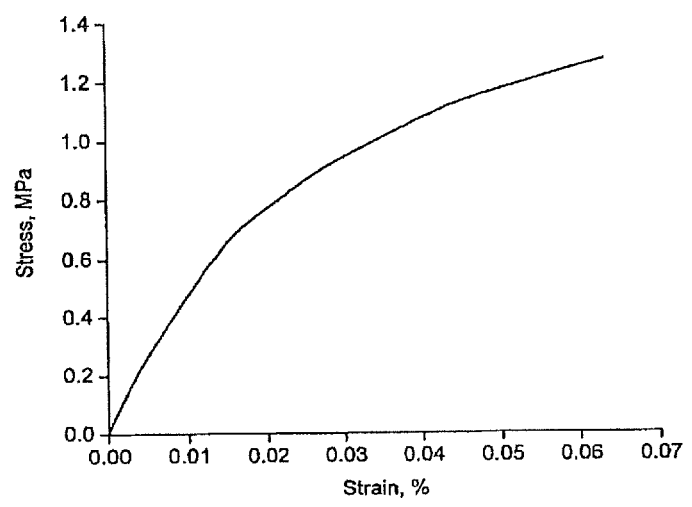
FIG. 20 depicts a Stress-strain curve of a bone-repair composite.

The stress-strain curve of the composite under small strain (<1%) is shown in FIG. 20 The Young's modulus is 6.5 GPa for linear region (0-0.001%).

Figure 21:
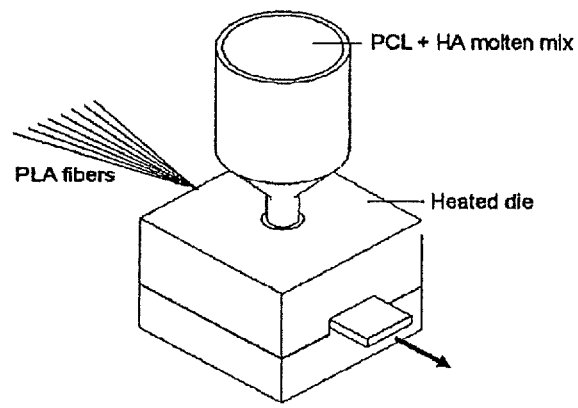
FIG. 21 depicts an apparatus used for pultrusion of composite.

A pultrusion process was also used to prepare the PLA-PCL-HA composite. PLA fibers were pulled through a tapered die filled with molten PCL-HA mixture, which has an HA:PCL volume ratio ranges from 0.1~0.2. The apparatus used for the pultrusion is shown in FIG. 21. The tensile test results were listed in Table 5.

TABLE 5

Tensile test results of pultruded composite

| Composition (volume %) | | | |
|---|---|---|---|
| PLA | PCL | HA | Young's modulus (GPa) |
| 0.09 | 0.82 | 0.09 | 1.1 |
| 0.18 | 0.74 | 0.08 | 1.9 |
| 0.09 | 0.76 | 0.15 | 1.2 |
| 0.20 | 0.66 | 0.14 | 2.2 |

Figure 22:
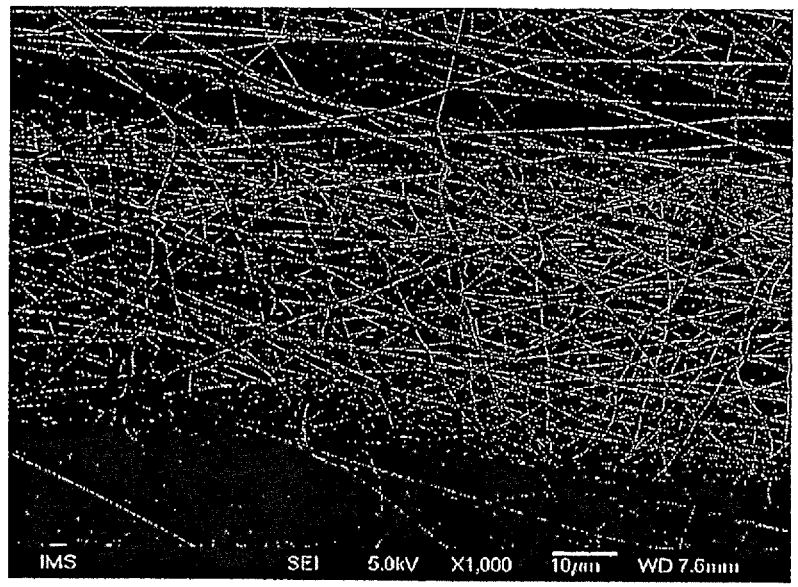
FIG. 22 illustrates the alignment of HA particles within PLLA fibers by electrospinning HA particles in a dimethylformamide solution.

Hydroxyapatite particles can also be aligned along the PLLA melt spun yarn by electrospinning HA particles in a solution of PLLA in dimethylformamide over melt spun PLLA yarn as shown in FIG. 22. The process is carried out by first winding PLLA yarn onto a grounded rotating wheel or drum and then electrospinning filaments containing HA particles over the PLLA yarn. HA particles with aspect ratios greater than about 4:1 tend to align themselves within the PLLA electrospun filaments. When the HA containing filaments are wound over the melt spun PLLA yarn, the amount of alignment of the HA particles with the PLLA yarn will be proportional to the alignment of the electrospun yarn with the melt spun yarn. Samples prepared by this method can then be coated and hot pressed.

Example 3

PLLA ($M_n$=1.21×10$^5$, MWD=1.29) yarns (30 denier, 25±2 μm) for samples I were pre-etched in 0.50 mol/L NaOH solution for 30 min at room temperature. After being rinsed with de-ionized water and air dried for 24 h, yarns I, II and III were coated with hydroxylapatite (HA) by a biomimetic method at 42° C. for 24, 12, and 24 h, respectively. As shown in Table 6, with NaOH etching pretreatment, sample I gained higher HA/PLLA weight ratio than both II and III. This suggested that thicker HA coating was obtain on the etched fiber (Sample I) because the initial specific surface of the yarns in all the three samples were the same. Also, sample III exhibited higher HA/PLLA weight ratio than that of sample II, indicating that a longer coating time gives a thicker coating.

TABLE 6

Comparison of composition and three point bending results of sample I, II and III

| 3PB Beam | PLLA wt % | HA wt % | PCLGA wt % | Max flexural stress/MPa | Flexural Modulus/GPa |
|---|---|---|---|---|---|
| I | 74.04 | 9.92 | 16.04 | 132 | 5.4 |
| II | 77.66 | 6.743 | 15.60 | 87 | 4.2 |
| III | 70.13 | 6.86 | 23.02 | 45 | 3.8 |

The HA-coated PLLA yarns were vacuum dried overnight before being dipped into poly(ε-caprolactone-co-glycolic acid) (PCL:PGA=90:10) acetone solution for 5-10 min, whose concentration was 10% w/v. PLLA/HA/PCLGA composites were dried under vacuum for 24 h, after which the composites were hot pressed using a flat die to form beams for three point bending tests.

The flexural stress and modulus of the PLLA/HA/PCLGA composite beams with a dimension of 30.0 mm×5.3 mm×2.0 mm are tested with a three-point bending test. At a strain rate of 5 mm/min, the flexural stress of sample I was found to be 132.2 MPa and its modulus is 5.4 GPa. Comparing these values with those of sample II, it could be found that, with similar weight percentage of PCLGA coating, sample I with higher amount of HA demonstrated better mechanical properties (higher flexural stress and modulus). When comparing flexural stress and modulus of samples II and III, it was found that sample II with lower amount of PCLGA demonstrated better mechanical properties, which could be attributed to much lower flexural strength and modulus of the amorphous PCLGA coating layer.

Braids

As used herein, a "braid" shall include any structure using a combination of elements that are arranged with an inner element and an outer element. A typical structure of a braid consists of the center part, the core 118, and the outside part, the sheath 120. This configuration and the technology for its manufacture are adapted to create a novel composite for delivering growth factors during bone repair. The advantage of braiding is that it allows precise placement of different fibers within the composite and variation of the fiber ratios over a large range.

In the present invention, the fibers at the core 118 are coated with calcium phosphate before braiding. In contrast, the sheath 120 is subjected to substantial twisting, bending and sliding during the braiding, so it is not coated with calcium phosphate. The core is assembled with the sheath of yarn braided over its surface to form a tubular braid (see FIGS. 17A, 17B, and 17C), which is used as a building block for constructing different implants or devices.

In accordance with an embodiment of the present invention, the polymer yarns with or without calcium phosphate coating form a primary unit of the braided structure, as show in FIGS. 17(a), (b), (c). The primary units form the core 118 and the sheath 120 of the braids, which are the secondary units of the structure. The calcium phosphate-coated yarns form the core 118, while the uncoated ones form the sheath 120. The sheath 120 may be subjected to substantial torsion and bending during the braiding, so it is not coat with calcium phosphate. Finally, the core secondary units are assembled with the sheath secondary unit braided over its surfaces, which is the tertiary unit of the structure. The tertiary unit is used as a building block for constructing different implants or devices. The composition of the primary unit is adjusted to achieve the mechanical and chemical properties meeting the requirements for different load bearing skeletal implants.

Fabrication A: Bar-Shaped Composite

FIG. 23 is a flowchart outlining an exemplary operation according to the present disclosure for the construction of the novel composite. In operation, the process starts at step 202, where the primary units, PLLA, PGA, PCL, and PDO yarns 102 are gathered. Next, in step 204, the primary units are coated with hydroxyapatite (CaP) to form coated fibers 104, and in turn form the core secondary units 118. In conjunction with step 204, in step 206, the primary units can form a sheath 120. The sheath 120 is not coated with hydroxyapatite (CaP).

Then, in step 208, an appropriate ratio of core secondary structure and the sheath secondary structure (from steps 204 and 206) are braided together to form a tertiary unit. Next, in step 210, the tertiary unit is dip-coated with PLC mixture and compression molded in elevated temperature. In step 212, the tertiary unit is subjected to mechanical testing.

Construction of the Primary Unit

Fibers:

Four synthetic biodegradable polymer fibers, poly(L-lactic acid) (PLLA), polyglycolic acid (PGA), poly(ε-caprolactone) (PCL) and polydioxanone (PDO), are used as in construction of the composites. The melting temperature, mechanical properties, degradation rate and accessibility to solvents of these fibers are listed in Table 7. The combination of these polymers covers a wide range of chemical, physical and morphological variables.

TABLE 7

The melting temperature, degradation rate, and accessibility to solvents of PGA, PDO, PLLA, PCL, and collagen fibers.

|  |  | PGA | PDO | PLLA | PCL |
|---|---|---|---|---|---|
| Melting temperature, ° C. |  | 225 | 109 | 175 | 60 |
| Young's Modulus (GPa) |  | 7.0 | 1.5 | 6.0-7.0 | 0.4 |
| Tensile strength (MPa) |  | 730 | 600 | 500-550 | 240 |
| 50% tensile strength loss |  | 14 days | 1 month | 18 months | — |
| 100% mass loss |  | 6-12 months | 6-12 months | >36 months | >24 months |
| Solvents | Toluene | Non-solvent | Non-solvent | Non-solvent | Solvent |
|  | Xylene | Non-solvent | Non-solvent | Non-solvent | Solvent |
|  | Ethyl acetate | Non-solvent | Non-solvent | Non-solvent | Solvent |
|  | Acetone | Non-solvent | Non-solvent | Non-solvent | Solvent |

FIGS. 17(a), (b), and (c) depict the composite construction of the novel composite according to the invention. As shown, a combination of catgut, PGA, and PLLA fibers 102/104 form the core of the braid 118, and the PLLA fibers form the sheath 120 of the suture braid 130. The large cylinders represent polymer braids 130 and small cylinders represent polymer yarns 102. FIG. 17A is a composite construction of the novel composite: a combination of PCL-coated PLLA 104, catgut 102b, and PGA 102c fibers form the core 118, PLLA 102 forms the sheath 120, and the braid 130 is then coated with PCL mixture 134. FIG. 17B illustrates that a porous structure at the core 118 is formed due to the early degradation of the catgut 102b. FIG. 17C further illustrates that with increasing the implantation time, PGA (102c) at the core degrades and creates more channels (white) in the structure.

According to the invention, the fibers 102 are pre-coated with calcium phosphate as described above. In some embodiments, the fibers at the core are coated with a mixture of PCL and glyceryl monostearate ($T_m$~50-70° C.). It is found that adding glyceryl monostearate in PCL increased the porosity of the composite, which could be used to controlled release of proteins. This is the first time the use of PCL and glyceryl monostearate mixture as a coating on polymer fibers for this purpose. In the rest of the constructions, the core is polymer-coating free. The PCL mixture is dissolved in an organic solvent, such as toluene, xylene, or ethyl acetate, which does not attack PLLA, PGA, or catgut fibers. The thickness of the coating is controlled by adjusting the concentration of the dipping solution, the coating speed, and the number of passes through the coating bath. The amount of the glyceryl monostearate in PCL is adjusted depending on the drug release rate requested.

In the fabrication of the composite, the ratio of core to sheath is maximized to improve the mechanical strength of the construction. The fibers at the core are aligned along the fiber axis providing a high Young's modulus contribution, while those in the sheath lie at an angle to the axis leading to reduction in contribution to the mechanical stiffness and strength of the composite. However, the preponderance of the fibers are in the core; thus, the braid still yields the composites with high mechanical strength. Upon the construction of the polymer braids, they are then coated with a layer of the mixture of PCL and glyceryl monostearate. The glyceryl monostearate acts as a crystallization modifier for the PCL. Other details of the dip-coating process are described above.

The polymer braids can be cut into the length of the compression mold, stacked up, and subjected to compression molding between 50-70° C. During the compression molding, the high melting temperature polymer yarns, such as PLLA ($T_m$=175° C.), PGA ($T_m$=225° C.), and catgut ($T_m$>200° C.), remain intact, while the low melting temperature PCL and glyceryl monostearate mixture coating ($T_m$=50-70° C.), melt and act as a "glue" to bind the yarns and the braids together (FIGS. 24A and 24AA). When the composite is implanted in vivo, the slow-degrading polymer fibers, such as PLLA and PGA, hold the structure of the composite, and provide the necessary mechanical strength during the bone healing. Meanwhile, the fast-degrading fibers, such as catgut, will degrade first and create a porous structure between the polymer yarns at the core (FIGS. 24B and 24BB). It will also release growth factors and induce bone ingrowth into the pores of the structure. Increasing implantation time, PGA will start to degrade, and create a more porous structure at the core and thereby inducing more bone ingrowth (FIGS. 24C and 24CC).

Construction of the Secondary and Tertiary Units 20-30 primary units are formed into a secondary unit. The core secondary unit 118 is coated with calcium phosphate, while the sheath 120 is calcium phosphate-free. In the construction of a tertiary unit, the ratio of core to sheath is maximized to improve the mechanical strength of the construction. The fibers at the core are aligned along the fiber axis providing a high Young's modulus contribution, while those in the sheath lie at an angle to the axis leading to reduction in contribution to the mechanical strength of the composite. The calcium phosphate-coated yarns at the core mimics the highly organized structure of osteon in natural bone, where collagen fibrils are aligned with nano-calcium phosphate platelets orientated along the fibril axis. Thus, the composite yields the polymer braids with a maximum mechanical strength.

In an embodiment, both the core 118 and the sheath 120 of the braid 130 are fabricated using a combination of the four polymer yarns available, PLLA, PCL, PDO and PGA. This yields composites with different microstructures, mechanical properties and drug release rates for load-bearing skeletal implants. Two composite fabrication techniques are employed to prepare the composites: hot compression molding and cold compression molding. In all of the experiments, a slot mold with positive displacement is used to make uniaxial composite samples. In an alternative embodiment, flow of the matrix material along the aligned fibers is allowed, leading to higher orientation of both the matrix and the fibers.

Hot Compression Molding

The polymer braids with various combinations at both the core and the sheath are cut into the length of the compression mold, stacked up, and subjected to hot compression molding. A compression molding temperature of 60-70° C. can be used. During the compression molding, the high melting temperature polymer yarns, such as PLLA ($T_m$=175° C.), PGA ($T_m$=225° C.), and PDO ($T_m$=109° C.), remain intact, while the low melting temperature PCL ($T_m$=60° C.) yarns melt and act as a "glue" to bind the braids together. An example of variety of constructions are built as listed below, these examples are illustrative and not meant to be limiting.

FIGS. 24 (a-d) depict various composite constructions after compressive molding (large cylinders represent polymer braids and small cylinders represent polymer yarns): (a) PLLA 102a as the core 118 and PCL 140 as the sheath 120, (b) a combination of PLLA 102a and PGA 102c or PDO 102d as the core 118 and PCL 140 as the sheath 120, (c) PLLA 102a as the core 118 and PGA 102c or PDO 102d as the sheath 120, and (d) PLLA 102a as the core 118 and the combination of PGA 102c and PDO 102d as the sheath 120.

Construction One

In an embodiment, the calcium phosphate-coated PLLA yarns 102a can be the core 118 of the braid 130, while the PCL yarns 140 can be the sheath 120. This design is the most basic construction among all the proposed structures. During the hot compression molding, the PCL at the sheath melts, penetrate into the calcium phosphate coating, and act as a "glue" to provide strong bonding of the calcium phosphate-coated PLLA braids. In contrast, the PLLA braids retain their structural integrity, become aligned, and bind together through the PCL melt (FIG. 24a).

Construction Two

In another embodiment, a combination of calcium phosphate-coated PLLA 102a and PGA 102c (or PDO 102d) yarns can be used as the core 118, while the PCL 140 yarns can form the sheath 120, as shown in FIGS. 24B and 24BB. A similar aligned structure is formed after compression molding as described in Construction one. In comparison to Construction two, the PGA (or PDO) yarns at the core will degrade much faster than PLLA when the composite is implanted in vivo, thereby resulting in many hollow column channels in the structure. These columns will facilitate the early stage bone ingrowth, while the PLLA yarns will remain structurally sound and loose strength over the long-term.

Construction Three

In another embodiment, the calcium phosphate-coated PLLA 102a yarns form the core 118 of the braid 130, while the uncoated PGA 102c can be the sheath 120, as shown in FIGS. 24C and 24CC. PCL dissolves in toluene, xylene, or ethyl acetate, which is a non-solvent for both PLLA and PGA. The braids are dip-coated with PCL, and dried in air. After compression molding, the PCL binds the polymer braids together. When this composite is implanted in vivo for a period, such as one month, a hollow shell around the PLLA core can be gradually formed due to the fast degradation of the PGA yarns, and the bone tissue can gradually grow into the shell during this period. The thickness of the shell can be controlled to achieve the optimum space to facilitate bone-ingrowth. In contrast, the PLLA core will remain aligned and supply the long-term mechanical strength for the implant. The whole implant will be finally replaced by the natural bone in approximately 2 years.

Construction Four

In another embodiment, the calcium phosphate-coated PLLA yarns 102a form the core 118 and a combination of PGA 102c and PDO 102d yarns form the sheath 120 of the construction, as shown in FIGS. 24D and 24DD. Like Construction three, the braids are dip-coated with PCL. After compression molding, the PCL binds all the braids together, while PGA and PDO remain holding the PLLA yarns at the core. After implanting in vivo for about two weeks, PGA will degrade, which will create a porous sheath to facilitate bone ingrowth. In the meantime, the PDO sheath will remain in place for an extra of two weeks, which will allow more time for bone tissue ingrowth.

Cold Compression Molding

Even temperatures as low as 60° C. might affect the crystalline structure of the PLLA, PGA or PDO fibers. Thus, it is desirable to work at even lower temperatures, such as room temperature. As indicated in Table 3, toluene, xylene, and ethyl acetate are good solvents for PCL but they do not attack PLLA and presumably do not alter its crystalline morphology. A similar construction to Construction One can be employed where PLLA yarns can be the core, and PCL yarns can be the sheath of the braid. The polymer braids can be cut to the length of the mold and stacked in the mold. One of the three solvents listed above can be added in vapor form to the polymer stack so as to soften the PCL yarns. The softened PCL sheath can bind all the polymer braids together during cold compression molding at temperatures much lower than 60° C. The cold compression molding can also be employed to form the structure in the rest of the constructions as the three solvents listed above are also non-solvent for PGA and PDO.

Fabrication B: Sheet-Shaped Composite

In another embodiment, the PLLA fibers can also be woven or knitted into a piece of cloth, and then coated with calcium phosphate. The growth factors can be incorporated into the lattice structure of the calcium phosphate coating or directly deposit on the surface of the coating. The growth factor-loaded fabric can be inserted at the interface of the sternal bones to improve their closure after the cardiovascular surgery. The sternal bone of the patient is cut into half during the cardiovascular surgery, and stainless steel wires are normally used to hold the sternum together during the bone healing process. Unfortunately, the patient suffers a lot of pain due to the use of the stainless steel wire. Plus, the stainless steel wire may cause inflammation at the surgery site. Consequently, the healing process is long and painful for the patient. If high strength polyethylene suture is used in combination with the present invention, not only the pain of the patient will be reduced due to the use of the high strength polyethylene suture, but also the bone healing rate will be accelerated significantly due to composite insertion.

The crystallinity of the PLLA and PGA phases in the resulting composite can be investigated by XRD and differential scanning calorimetry (DSC). As appropriate, transmission electron microscope (TEM) and small-angle x-ray scattering (SAXS) analyses can be added to characterize the calcium phosphate alignment and distribution in the polymer and crystalline morphology of the polymer. The surface morphology of the composite can be assessed using environmental scanning electron microscopy (ESEM).

Mechanical Testing

The synergistic effect of using bone-like calcium phosphate precipitated on the surface of highly aligned polymer fibers, appropriate calcium phosphate loadings, and optimum processing conditions should improve the mechanical properties of the composite dramatically. The tensile and flexural tests can be conducted on the composites according to ASTM D638 and D790-02, respectively, and the Young's modulus and Poisson's ratio can be determined. Before mechanical testing, the samples can be cut into standard geometries for each test. The data can be compared with the mechanical properties of the cortical bone (tensile strength: 60-160 MPa; Young's modulus: 3-30 GPa; shear modulus: 3.5 GPa; Poisson's ratio: 0.25) as well as with other composites designed for orthopedic applications.

In Vitro Test

To understand the effect of different polymer constructions on bone formation rate on the composites, an in vitro cell culture study can be carried out. The composites of each construction with the optimum processing conditions can be subjected to cell culture study. Alkaline phosphatase (ALP), mineral deposition, and bone nodule formation are three important markers at different stages of bone formation in vitro. In the present invention, ALP, calcium deposition, and bone nodule formation assays are performed to reveal the optimum combination of polymers for bone formation.

Cell Attachment, Proliferation, ALP, Calcium Deposition, and Bone Nodule Formation A rat osteosarcoma cell line can be used in the proposed study, as the cells are calcified easily in vitro. The interactions between osteoblasts and different composites can be investigated. Cell attachment, proliferation and ALP activities can be performed on the surface of the composites. Tissue culture plastics can be used as controls, which have cells alone in the culture without any composite. The cell attachment can be carried out at different time points, such as 1, 3, 5 and 8 hours, using an alamarBlue fluorescent Dye™ technique. An optimum time point for cell attachment can be determined. Following cell attachment, osteoblasts undergo a high level of proliferation. The rate of proliferation can indicate the success of a substrate at promoting osteoblast growth. The same alamarBlue Dye™ technique can be utilized in assessing the cell proliferation rate. Osteoblast proliferation can be determined on days 1, 3, and 7. The cell morphology can be observed using scanning electron microscopy (SEM). After a slightly longer incubation period, such as 17-21 days, calcium deposition proceeds. The calcium measurements can be undertaken using calcium crimson (a dye that stains calcium) and acridine orange staining followed by confocal microscopy observation. Bone nodule formation can be detected using von Kossa staining. Images can be taken using an optical microscope.

Statistical Analysis:

A statistical analysis can also be conducted. Statistical significance can be determined using a one-way of variance (ANOVA) to compare means between groups, with a P value of less than 0.05 being considered significant.

Controlled Release of Drugs

Introduction

Almost all the components, including the biomimetically formed calcium phosphate, the PLLA, PGA and catgut fibers, and the PCL mixture coating in the proposed composite can be used as delivery carriers, which makes it possible to incorporate multi-growth factors into the structure. Controlled release can be achieved by varying the composite constructions, using different drug incorporation methods to add growth factors into different carrier components of the composite. In addition, due to the unique design of the composite structure, while the fast-degrading polymers break down, the slow-degrading polymers can maintain the mechanical strength of the composite. Such a system can be ideal in conducting more sophisticated drug delivery.

In the present invention, two drug-delivery systems: single- and multi-drug are disclosed. Both in vitro and in vivo studies are carried out to demonstrate a sustained and stable controlled release of drugs, as needed for optimum bone healing. In the in vitro model, a single drug delivery system is investigated to learn about the release properties of the composites and their components, with the aim of achieving an optimum drug release profile. In the in vivo study, both single- and multiple-drug delivery systems are studied.

In Vitro Study

Growth factor(s) are incorporated into different compartments of the composite to provide sequential release. This unique characteristic of the system can be used to design a more sophisticated drug-release system. A systematic study is carried out to investigate the effect of the degradation rate, the drug incorporation method, and the crystallinity of the polymers on the drug release rate of the constructed composites.

A Single-Component Carrier System

In one embodiment of the present invention, BMP-2 is released by one of the following three carriers: 1) polymer fibers, 2) PCL mixture coatings, and 3) calcium phosphate coatings. A total dose of 21 µg rhBMP-2 is placed on each implant based on previous experience. For the polymer fibers (including PLLA, PGA, and catgut fibers), the BMP is directly deposited on the surface of these fibers and the release profile of the BMP is measured by BCA protein assay. To measure the BMP release, the polymer fibers is suspended in a N,N-bis(2-hydroxyethyl)-2-aminoethanesulfonic acid (BES) buffer for different time periods up to 8 weeks at 37° C. They are then be removed from the solution, and the supernatant is evaluated by a BMP-2 enzyme-linked immunoadsorbent assay (ELISA).

In the case of PCL mixture coatings, the BMP is added to the coating solution and applied on the surface of BMP-free PLLA fibers. The glyceryl monostearate content in PCL vary between 0-10 wt % to alter the protein release rate in the coating. The release rate is increased with the content of glyceryl monostearate in the PCL as the porosity of the coating increases. For the calcium phosphate coating, BMP is incorporated into its lattice structure to create a sustained release profile. Briefly, BMP is added into the simulated body fluid solution, and co-precipitate with the calcium phosphate on the surface of the polymer. It is noted that only about 50% of the BMP had released after 5 weeks of implantation when BMP was incorporated into the lattice structure of calcium phosphate, but no release was observed at the first week of implantation. Finally, the BMP incorporated polymer braids are subjected to compression molding between 50-70° C., at which temperature most of the growth factors can survive.

A Multiple-Component Carrier System

In one of the embodiments, a sustained steady controlled release profile is designed using sequential release of the growth factor from different components of the composite. First, a low dose of BMP can be incorporated into a component with a fast releasing rate, such as catgut and PGA. Since a low dose is used, the "burst release" of the BMP won't create a local overdose effect. Second, the rest of the BMP can be incorporated into a component with a slow releasing rate, such as the calcium phosphate or the PCL mixture coating. It is hypothesize that a two-step sequential release can ensure a steady release started from day 0, and can last for up to 8 weeks. Such created release profile can be ideal for the human bone healing, which normally takes 2-3 months. It should be noted that drug release rate of the fast-degrading polymer may slow down due to the PCL mixture coating on its surface.

Measurement and Modeling of Release Kinetics

The proposed composites are at one time complex and simple. The geometry comprising yarns of different compositions and braids of different constructions embedded in a matrix with various filler loadings, is a complication. The macro sample size and the pseudo one-dimensional geometry are simplifying aspects of the problems of measuring and modeling degradation and drug-release kinetics. The high molecular weight of the growth factor is also a simplification in that it is hypothesized its solubility and diffusivity in the matrix will be vanishingly low. To study the release kinetics of the biodegrading composite, the following factors will be examined:

Influence of plasticization of the matrix on molecular diffusion;

Influence of molecular weight during degradation on molecular diffusion;

Combined degradation and molecular diffusion; and

Diffusion from porous, degrading solids.

The release profiles, i.e., release rate vs. time, of the composites can vary significantly, but the studies cited here were essentially "take what you get" from the point of view of controlling the profile in a predictive fashion. In addition, the added complication of diffusion limitations brought about by growing bone tissue has not been addressed adequately.

With the composites proposed, growth factor release rate can be precisely controlled because of the flexibility in composition and structure. For simplicity of analysis, cylindrical composite rods can be subjected to one-dimensional degradation by capping the rod ends with epoxy. At the end of the degradation time, the rod can be sectioned and its morphology studied with spatially resolved surface techniques and the standard portfolio of morphological analyses using scanning electron microscope, optical microscope and atomic force microscope, as appropriate. In addition, bulk properties (molecular weight, drug concentration) can be studied by radial profiling followed by standard solution analyses.

Modeling of the degradation kinetics will follow the example of Lemaire et al., but with changes to incorporate the unique geometries of the composites. Of somewhat incidental importance, but nevertheless interesting, is that release along the axis of the composites, i.e., from the ends, is a model situation for the analysis of Lemaire et al.

In Vivo Study:

The composite with the optimum release profile and reasonable mechanical strength will be used for the in vivo studies. Once it is certain that BMP is being stored and released from the three different compartments of the composite, as determined with in vitro tests, then single vs. multiple agent delivery can be compared in vivo. Applying current understanding of normal wound repair, combinations of growth factors have great potential to enhance healing as bone formation and repair are regulated by many factors, including extracellular matrix and several growth factors. In natural, these growth factors participate in the bone repair at different sequences. A preliminary in vivo study will be carried out using a mouse model. Sixty mice each will receive four implants (two controls and two specimens) placed directly at both the calvarie and ectopic sites. It is important to have implants at both the calvarie and the ectopic sites, as the bone healing is much easier at the former site than the later. It is known that the bone-healing rate of mouse is much faster than that of human being, so it will be beneficial to have two implantation sites in the mouse model to test the bone forming induced by different drug delivery systems.

The composite without growth factors will be used as the control. 20 mice receive rhBMP-2 alone, 20 receive the combination of both rhBMP-2 and TGF-β with rhBMP-2 releasing first, and the rest 20 also receive the combination of the two drugs but with TGF-β releasing first. A dose of 21 µg of rhBMP-2 is placed on each implant, which receives rhBMP-2 alone, while 21 µg of rhBMP-2 and 2 µg TGF-β are placed on the implant for combined release based on previous research. The mice are sacrificed at 1, 2, 21, and 42 days after implant placement, and 5 mice at each time point are used in the study, for a total of 60 mice.

Samples containing the implants and surrounding tissues are harvested and fixed in 10% neutral-buffered formalin. Following fixation, the samples are analyzed by computer-aided microtomography (microCT) at a resolution of 12 µm (µCT40, Scanco Medical AG, Bassersorf, Switzerland) to assess the amount of new bone height, volume, bone mineral density and microarchitecture of new bone adjacent to each test implant for this study.

For the most part, the factors (materials, designs, process methods, system thermodynamic variables) are examined using straight-forward factorial designs that are analyzed using standard analysis of variance (ANOVA) and multi-variant linear modeling methods.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A bone replacement composite comprising:
   a poly(ε-caprolactone) (PCL) matrix;
   a multitude of poly(L-lactic) acid (PLLA) fibers disposed within the PCL matrix, the multitude of PLLA fibers being aligned along a common axis; and
   a calcium phosphate mineral layer coating each of the PLLA fibers, the calcium phosphate mineral layer being between 25% by weight and 43% by weight of the bone replacement composite, wherein a crystalline orientation of the calcium phosphate mineral layer is aligned with the common axis, wherein the bone replacement composite is a rod or bar-shaped composite configured to replace a portion of a bone in a patient and wherein a bending modulus of the bone-repair composite is at least 3 GPa.

2. The bone replacement composite according to claim 1, wherein a ratio of PLLA fibers to PCL matrix is 6:1 wt/wt.

3. The bone replacement composite according to claim 2, further comprising filing materials including drugs or bioactive agents, wherein the filling materials is used as a binding material or for drug release.

4. The bone replacement composite according to claim 2, further comprising fibers made from materials selected from a group consisting of collagen, hyaluronans, fibrin, chitosan, alginate, silk, polyesters, polyethers, polycarbonates, polyamines, polyamides, co-polymers, polyglycolic acid (PGA), poly(D,L-lactide-coglycolide) (PLGA), and poly(ε-caprolactone) (PCL).

5. The bone replacement composite according to claim 2, wherein the calcium phosphate mineral layer is selected from a group consisting of ion-substituted apatite, calcium phosphate, carbonate hydroxyapatite, fluorinated hydroxyapatite, chlorinated hydroxyapatite, silicon-containing hydroxyapatite, tricalcium phosphate, tetracalcium phosphate, monotite, dicalcium phosphate, dicalcium phosphate dihydrate, octacalcium phosphate, calcium phosphate monohydrate, alpha-tricalcium phosphate, beta-tricalcium phosphate, amorphosus calcium phosphate, biphasic calcium phosphate, calcium deficient hydroxyapatite, precipitated hydroxyapatite, and oxyapatite.

6. The bone replacement composite according to claim 2, wherein the calcium phosphate mineral layer is anchored to the polymer surface by electrostatic, coordinative, ionic or chemical tethering.

* * * * *